United States Patent
Tojo et al.

(10) Patent No.: US 11,161,126 B2
(45) Date of Patent: Nov. 2, 2021

(54) METHOD FOR PRODUCING FILM

(71) Applicant: Kao Corporation, Tokyo (JP)

(72) Inventors: Takehiko Tojo, Utsunomiya (JP); Ikuo Fukuda, Chikusei (JP)

(73) Assignee: Kao Corporation, Tokyo (JP)

( * ) Notice: Subject to any disclaimer, the term of this patent is extended or adjusted under 35 U.S.C. 154(b) by 125 days.

(21) Appl. No.: 16/606,380

(22) PCT Filed: Apr. 19, 2018

(86) PCT No.: PCT/JP2018/016216
§ 371 (c)(1),
(2) Date: Oct. 18, 2019

(87) PCT Pub. No.: WO2018/194143
PCT Pub. Date: Oct. 25, 2018

(65) Prior Publication Data
US 2020/0038891 A1 Feb. 6, 2020

(30) Foreign Application Priority Data

Apr. 19, 2017 (JP) .............................. JP2017-083247
Apr. 19, 2017 (JP) .............................. JP2017-083248
Apr. 19, 2017 (JP) .............................. JP2017-083249

(51) Int. Cl.
*B05D 1/04* (2006.01)
*B05D 1/06* (2006.01)
(Continued)

(52) U.S. Cl.
CPC ............ *B05B 5/1675* (2013.01); *A45D 34/04* (2013.01); *A61K 8/046* (2013.01); *A61Q 1/00* (2013.01);
(Continued)

(58) Field of Classification Search
CPC . A61Q 1/02; A61Q 1/12; A61Q 19/00; A61Q 15/00; A61Q 17/04; B05D 1/007;
(Continued)

(56) References Cited

U.S. PATENT DOCUMENTS 3,857,233 A    12/1974  Cardinal et al.
4,125,752 A    11/1978  Wegener
(Continued)

FOREIGN PATENT DOCUMENTS

EP    3 366 270 A1    8/2018
EP    3 375 323 A1    9/2018
(Continued)

OTHER PUBLICATIONS

International Search Report dated Jun. 26, 2018 in PCT/JP2018/016216 filed Apr. 19, 2018.
(Continued)

*Primary Examiner* — Alexander M Weddle
(74) *Attorney, Agent, or Firm* — Oblon, McClelland, Maier & Neustadt, L.L.P.

(57) ABSTRACT

A method for producing a film of the present invention includes an electrostatic spraying step of electrostatically spraying a liquid composition directly on the surface of skin to form a film on the skin by using an electrostatic spray device. The electrostatic spray device includes a container capable of storing the liquid composition, a nozzle configured to eject the liquid composition, and a power supply configured to apply a voltage to the nozzle. The liquid composition contains component (a): one or two or more volatile substances selected from alcohols and ketones, component (b): a water-insoluble polymer having film formability, and component (c): 0.2% by mass or more and 25% by mass or less of water.

16 Claims, 3 Drawing Sheets

(51) Int. Cl.
*B05B 5/16* (2006.01)
*A45D 34/04* (2006.01)
*A61K 8/04* (2006.01)
*A61Q 1/00* (2006.01)
*A45D 34/00* (2006.01)
*B05D 1/00* (2006.01)

(52) U.S. Cl.
CPC .............. *B05B 5/1691* (2013.01); *B05D 1/04* (2013.01); *B05D 1/06* (2013.01); *A45D 2034/005* (2013.01); *A45D 2200/057* (2013.01); *B05D 1/007* (2013.01)

(58) Field of Classification Search
CPC . B05D 1/005; B05D 1/04; A61K 8/34; A61K 2800/95; A61K 8/73; A61K 8/046; D01D 5/0061; D01D 1/0038; D01D 1/0084; B05B 5/006; B05B 5/007; B05B 5/053; B05B 5/1691; A61M 35/00
See application file for complete search history.

(56) References Cited

U.S. PATENT DOCUMENTS

| | | | |
|---|---|---|---|
| 5,322,684 A | 6/1994 | Barnett et al. | |
| 5,945,111 A | 8/1999 | Esser | |
| 6,135,369 A | 10/2000 | Prendergast et al. | |
| 6,311,903 B1 | 11/2001 | Gaw et al. | |
| 6,461,626 B1 * | 10/2002 | Rabe .................. | A61K 8/29 424/401 |
| 6,514,504 B1 | 2/2003 | Yen et al. | |
| 6,531,142 B1 | 3/2003 | Rabe et al. | |
| 7,105,058 B1 | 9/2006 | Sinyagin | |
| 2005/0212879 A1 | 9/2005 | Chiao et al. | |
| 2007/0131805 A1 | 6/2007 | Yamaguchi et al. | |
| 2009/0200392 A1 | 8/2009 | Duru et al. | |
| 2018/0317627 A1 * | 11/2018 | Fukuda .................. | B05B 12/084 |
| 2019/0053602 A1 | 2/2019 | Amari et al. | |
| 2019/0059551 A1 | 2/2019 | Amari et al. | |

FOREIGN PATENT DOCUMENTS

| | | | |
|---|---|---|---|
| JP | 2-78457 A | 3/1990 | |
| JP | 5-192224 A | 8/1993 | |
| JP | 2000-505356 A | 5/2000 | |
| JP | 2003-506474 A | 2/2003 | |
| JP | 2003-507166 A | 2/2003 | |
| JP | 2006-95332 A | 4/2006 | |
| JP | 2006-104211 A | 4/2006 | |
| JP | 2012-107364 A | 6/2012 | |
| JP | 2015-3293 A | 1/2015 | |
| JP | 2016-43306 A | 4/2016 | |
| JP | 2017-78062 A | 4/2017 | |
| JP | 2017-78063 A | 4/2017 | |
| WO | WO 94/11119 A1 | 5/1994 | |
| WO | WO 98/03267 A1 | 1/1998 | |
| WO | WO 01/12139 A1 | 2/2001 | |
| WO | WO 01/12335 A1 | 2/2001 | |
| WO | WO 03/072263 A1 | 9/2003 | |
| WO | WO 2005/075095 A1 | 8/2005 | |
| WO | WO-2017082179 A1 * | 5/2017 | ............... A61Q 1/02 |

OTHER PUBLICATIONS

International Search Report dated Jun. 12, 2018 in PCT/JP2018/016204, 2 pages.

Extended European Search Report dated Dec. 14, 2020 in European Patent Application No. 18787349.2, 10 pages.

U.S. Appl. No. 16/606,373, filed Oct. 18, 2019, US 2020-0129786 A1, Tojo, T., et al.

* cited by examiner

METHOD FOR PRODUCING FILM

CROSS REFERENCE TO RELATED APPLICATIONS

This application is a national phase application of PCT/JP2018/016216, filed Apr. 19, 2018, which claims priority to Japanese Patent Application No. 2017-083247, filed Apr. 19, 2017; Japanese Patent Application No. 2017-083248, filed Apr. 19, 2017; and Japanese Patent Application No. 2017-083249, filed Apr. 19, 2017, wherein the entire content and disclosure of each of the foregoing applications is incorporated by reference herein into the present application.

TECHNICAL FIELD

The present invention relates to a method for producing a film.

BACKGROUND ART

Various methods of forming a film by electrostatic spraying have been known. For example, Patent Literature 1 discloses a method of treating skin, and the method includes electrostatically spraying a composition on the skin. The composition used in the method contains a liquid insulating material, a conductive material, a particulate material, and a thickener. The composition is typically a cosmetic containing a pigment or a skin care composition. Specifically, a cosmetic foundation is used as the composition. In other words, the invention according to Patent Literature 1 is intended to electrostatically spray a cosmetic foundation for beauty to thereby make up the skin.

Patent Literature 2 discloses a disposable cartridge used for an electrostatic spray device of cosmetics. The electrostatic spray device is a hand-held, self-contained device. The electrostatic spray device is used for spraying a cosmetic foundation as with Patent Literature 1.

Patent Literature 3 discloses a method of electrohydrodynamically forming a solid or gel substance containing a material having a biological activity on skin and a device used therefor. The device is a hand-held, portable device.

Patent Literature 4 intends stable mass production of nanofibers and discloses a method for producing nanofibers involving discharging and spinning a polymer solution under high-voltage application and a production device therefor.

CITATION LIST

Patent Literatures

Patent Literature 1: WO 01/12139 A1
Patent Literature 2: WO 01/12335 A1
Patent Literature 3: WO 98/03267 A1
Patent Literature 4: JP 2012-107364 A

SUMMARY OF INVENTION

The present invention provides a method for producing a film, and the method includes an electrostatic spraying step of electrostatically spraying a liquid composition directly on a surface of skin to form a film on the skin by using an electrostatic spray device. The electrostatic spray device includes
  a container capable of storing the liquid composition,
  a nozzle configured to eject the liquid composition, and
  a power supply configured to apply a voltage to the nozzle.

The liquid composition contains component (a), component (b), and component (c):
  (a) one or two or more volatile substances selected from alcohols and ketones,
  (b) a water-insoluble polymer having film formability, and
  (c) 0.2% by mass or more and 25% by mass or less of water In the electrostatic spraying step, the power supply applies a voltage of 5 kV or more and 50 kV or less to the nozzle that ejects the liquid composition at a flow rate of 0.4 mL/h or more and 30 mL/h or less to perform electrostatic spraying on the surface of the skin, and a ratio of the flow rate F (mL/h) to the voltage P (kV) (flow rate F/voltage P) is 0.8 or less.

DESCRIPTION OF EMBODIMENTS

Figure 1:
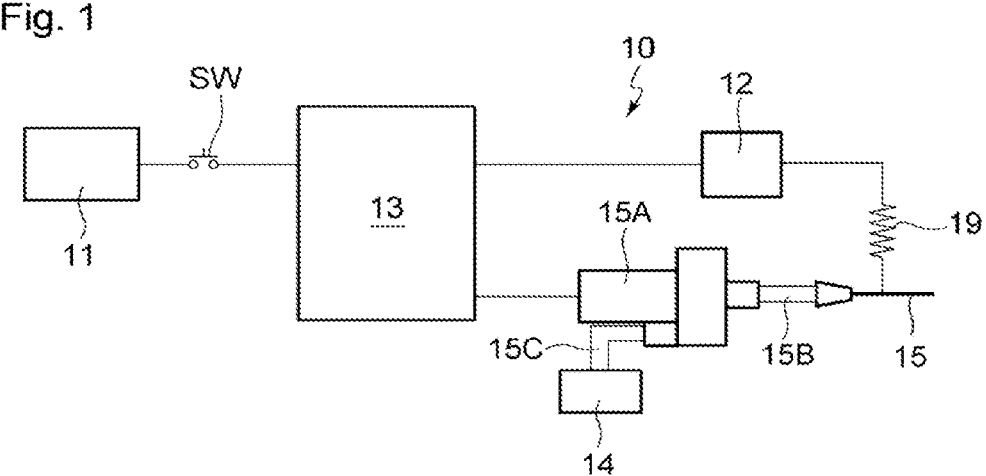
FIG. 1 is a schematic view showing the configuration of an electrostatic spray device used in the present invention.

When electrostatic spraying is performed to form a film on skin by the methods according to Patent Literatures 1 to 3, the film formed by the electrostatic spraying insufficiently adheres to the skin and may be damaged or peel off by an external force including friction. During film formation, the voltage applied to the film-forming liquid may be destabilized by the effect of ambient environment conditions including humidity, and this makes it difficult to stably form a film on skin. In addition, Patent Literatures include no description of insulating properties ensured when electrostatic spraying is performed.

The method according to Patent Literature 4 is for industrial production, and thus when electrostatic spraying is performed in accordance with the method in Patent Literature 4 to form a film on skin in a home or the like, where ambient environment conditions including humidity during production is difficult to control as compared with in factories, a stable voltage is failed to be applied in electrostatic spraying, and stable formation of a film on skin may be difficult.

The present invention therefore relates to a method of forming a film with a stable quality independent of an ambient environment including humidity while insulating properties are ensured at the time of electrostatic spraying.

The present invention will now be described on the basis of preferred embodiments thereof with reference to drawings. In the present invention, a composition containing prescribed components is applied directly onto skin to form a film. As the film formation method, an electrostatic spraying method is adopted in the present invention. In the electrostatic spraying method, a positive or negative high voltage is applied to a composition to electrically charge the composition, and the electrically charged composition is sprayed toward an object. The sprayed composition spreads in space while repeating miniaturization by the Coulomb repulsion. During this process or after the adhesion to an object, a solvent, which is a volatile substance, volatilizes, and a film is formed on the surface of the object.

In the present invention, the composition used in the electrostatic spraying method is liquid in an environment where the electrostatic spraying method is performed (hereinafter, the composition is also called "liquid composition"). The liquid composition contains the following component (a) and component (b):

(a) one or more volatile substances selected from the group consisting of alcohols and ketones; and (b) a polymer having film formability.

Hereinafter, the components will be described.

The volatile substance as the component (a) is a substance having volatility in a liquid state. In the liquid composition, the component (a) is contained for the following intention: the liquid composition in an electric field is sufficiently electrically charged and then is ejected from the tip of a nozzle toward skin; as the component (a) evaporates, the charge density of the liquid composition becomes excessive and thus the liquid composition is further miniaturized by Coulomb repulsion while the component (a) further evaporates; and consequently a dried film is formed. For this intention, the volatile substance preferably has a vapor pressure at 20° C. of 0.01 kPa or more and 106.66 kPa or less, more preferably 0.13 kPa or more and 66.66 kPa or less, even more preferably 0.67 kPa or more and 40.00 kPa or less, and further preferably 1.33 kPa or more and 40.00 kPa or less.

As the alcohol for the volatile substance as the component (a), for example, a monohydric chain aliphatic alcohol having 1 to 6 carbon atoms, a monohydric alicyclic alcohol having 3 to 6 carbon atoms, or a monohydric aromatic alcohol is suitably used. Specific examples thereof include ethanol, isopropyl alcohol, butyl alcohol, phenylethyl alcohol, propanol, and pentanol. One or more alcohols selected from these alcohols may be used.

As the ketone for the volatile substance as the component (a), for example, a chain aliphatic ketone having 3 to 6 carbon atoms, an alicyclic ketone having 3 to 6 carbon atoms, or an aromatic ketone having 8 to 10 carbon atoms is suitably used. Specific examples thereof include acetone, methyl ethyl ketone, methyl isobutyl ketone, cyclohexanone, and acetophenone. These ketones may be used singly or in combination of two or more of them.

The volatile substance as the component (a) is more preferably one or more substances selected from ethanol, isopropyl alcohol, butyl alcohol, and water, more preferably one or more substances selected from ethanol and butyl alcohol, and even more preferably ethanol.

The liquid composition contains, together with the component (a), a polymer having film formability as the component (b). The polymer having film formability as the component (b) is typically a substance capable of being dissolved in the volatile substance as the component (a). Here, "being dissolved" means that a substance is in a dispersion state at 20° C., and that the dispersion state is a visually uniform state, preferably a visually transparent or translucent state.

As the polymer having film formability, an appropriate polymer is used according to the properties of the volatile substance as the component (a). Specifically, the polymer having film formability is roughly classified into a water-soluble polymer and a water-insoluble polymer. The "water-soluble polymer" herein has the following properties: when 1 g of a polymer is weighed in an environment at 1 atmosphere and 23° C. and then is immersed in 10 g of ion-exchanged water for 24 hours, 0.5 g or more of the immersed polymer is dissolved in water. The "water-insoluble polymer" herein has the following properties: when 1 g of a polymer is weighed in an environment at 1 atmosphere and 23° C. and then is immersed in 10 g of ion-exchanged water for 24 hours, more than 0.5 g of the immersed polymer is not dissolved.

Examples of the water-soluble polymer having film formability include mucopolysaccharides such as pullulan, hyaluronic acid, chondroitin sulfate, poly-γ-glutamic acid, modified cornstarch, β-glucan, glucooligosaccharides, heparin, and keratosulfate; natural polymers such as cellulose, pectin, xylan, lignin, glucomannan, galacturonic acid, psyllium seed gum, tamarind seed gum, gum arabic, gum tragacanth, soybean water-soluble polysaccharides, alginic acid, carrageenan, laminaran, agar (agarose), fucoidan, methyl cellulose, hydroxypropyl cellulose, and hydroxypropyl methyl cellulose; and synthetic polymers such as a partially saponified polyvinyl alcohol (when used in combination with no crosslinking agent), a low-saponified polyvinyl alcohol, polyvinylpyrrolidone (PVP), polyethylene oxide, and sodium polyacrylate. These water-soluble polymers can be used singly or in combination of two or more of them. Of these water-soluble polymers, pullulan or a synthetic polymer such as a partially saponified polyvinyl alcohol, a low-saponified polyvinyl alcohol, polyvinylpyrrolidone, and polyethylene oxide is preferably used in view of easy production of a film. When used as the water-soluble polymer, the polyethylene oxide preferably has a number average molecular weight of 50,000 or more and 3,000,000 or less and more preferably 100,000 or more and 2,500,000 or less.

Examples of the water-insoluble polymer having film formability include a completely saponified polyvinyl alcohol that is to be insolubilized after film formation, a partially saponified polyvinyl alcohol that it to be crosslinked with a crosslinking agent after film formation, an oxazoline-modified silicone such as a poly(N-propanoylethyleneimine)-grafted dimethyl siloxane/γ-aminopropylmethylsiloxane copolymer, polyvinylacetal diethylaminoacetate, zein (major component of corn protein), polyester, polylactic acid (PLA), an acrylic resin such as a polyacrylonitrile resin and a polymethacrylate resin, a polystyrene resin, a polyvinyl butyral resin, a polyethylene terephthalate resin, a polybutylene terephthalate resin, a polyurethane resin such as polyurethane-64, a polyamide resin, a polyimide resin, and a polyamide imide resin. These water-insoluble polymers can be used singly or in combination of two or more of them. Of these water-insoluble polymers, a completely saponified polyvinyl alcohol that is to be insolubilized after film formation, a partially saponified polyvinyl alcohol that it so be crosslinked with a crosslinking agent after film formation, a polyvinyl butyral resin, a polymethacrylate resin, polyvinylacetal diethylaminoacetate, an oxazoline-modified silicone such as a poly(N-propanoylethyleneimine)-grafted dimethylsiloxane/γ-aminopropylmethylsiloxane copolymer, polylactic acid, zein, or the like is preferably used.

In the liquid composition, the content of the component (a) is preferably 50% by mass or more, more preferably 55% by mass or more, even more preferably 60% by mass or more, and further preferably 65% by mass or more. The content is preferably 95% by mass or less, more preferably 94% by mass or less, even more preferably 93% by mass or less, and further preferably 92% by mass or less. In the liquid composition, the content of the component (a) is preferably 50% by mass or more and 95% by mass or less, more preferably 55% by mass or more and 94% by mass or less, even more preferably 60% by mass or more and 93% by mass or less, and further preferably 65% by mass or more and 92% by mass or less, or is preferably 55% by mass or more and 92% by mass or less. The liquid composition having a content of the component (a) within the range described above can be sufficiently volatilized when the electrostatic spraying method is performed.

In the liquid composition, the content of the component (b) is preferably 1% by mass or more, more preferably 2% by mass or more, even more preferably 3% by mass or more, and further preferably 5% by mass or more. The content of the component (b) is preferably 40% by mass or less, and when the component (b) contains polyvinyl butyral, the content is preferably 35% by mass or less, more preferably 30% by mass or less, and even more preferably 25% by mass or less. In the liquid composition, the content of the component (b) is preferably 1% by mass or more and 40% by mass or less, is preferably 1% by mass or more and 35% by mass or less, more preferably 2% by mass or more and 35% by mass or less, even more preferably 3% by mass or more and 30% by mass or less, and further preferably 5% by mass or more and 25% by mass or less, or is preferably 5% by mass or more and 40% by mass or less. When the liquid composition has a content of the component (b) within the range described above, an intended film can be successfully formed.

The liquid composition preferably contains, in addition to the component (a) and the component (b), water as component (c). As the water, ion-exchanged water, purified water, or distilled water is suitably used.

When the liquid composition contains water as the component (c), the liquid composition has a higher conductivity due to ionization of water. When the liquid composition having a high conductivity is used to perform the electrostatic spraying described later, a fibrous film can be stably formed on the surface of an application site such as skin. Water also contributes to an improvement in adhesion of a film formed by electrostatic spraying to skin or the like.

In view of exhibiting such advantageous effects, the content of the component (c) in the liquid composition is preferably 0.2% by mass or more and 25% by mass or less. From the same viewpoint, the content of the component (c) in the liquid composition is preferably 0.3% by mass or more, more preferably 0.35% by mass or more, and even more preferably 0.4% by mass or more. In the liquid composition, the content of the component (c) is preferably 25% by mass or less, more preferably 20% by mass or less, even more preferably 19% by mass or less, and further preferably 18% by mass or less, in view of stable formability of a fibrous film. In the liquid composition, the content of the component (c) is preferably 0.2% by mass or more and 25% by mass or less, more preferably 0.3% by mass or more and 20% by mass or less, even more preferably 0.35% by mass or more and 19% by mass or less, and further preferably 0.4% by mass or more and 18% by mass or less, or is further preferably 0.3% by mass or more and 18% by mass or less.

From the viewpoint of stable film formation by the electrostatic spraying method, the content mass ratio of the component (a) to the component (c) (a/c) is preferably 3 or more, more preferably 3.5 or more, and even more preferably 4 or more. The content mass ratio of the component (a) to the component (c) (a/c) is preferably 300 or less, more preferably 250 or less, and even more preferably 210 or less. The content mass ratio of the component (a) to the component (c) (a/c) is preferably 3 or more and 300 or less, more preferably 3.5 or more and 250 or less, even more preferably 4 or more and 250 or less, and furtherly 4 or more and 210 or less.

From the same viewpoint, the mass ratio of the content of the component (b) to that of the component (c), b/c, is preferably 0.4 or more, more preferably 0.5 or more, and even more preferably 0.6 or more. The mass ratio of the content of the component (b) to that of the component (c), b/c, is preferably 140 or less, and when the component (b) contains polyvinyl butyral, the ratio is preferably 50 or less, more preferably 45 or less, and even more preferably 40 or less. The mass ratio of the content of the component (b) to that of the component (c), b/c, is preferably 0.4 or more and 140 or less, or is preferably 0.4 or more and 50 or less, more preferably 0.5 or more and 45 or less, and even more preferably 0.6 or more and 40 or less, or is preferably 0.6 or more and 140 or less.

From the viewpoint of the dispersibility of the component (b) in the liquid composition and of an improvement of film formability, the mass ratio of the component (b) to the component (a) (b/a) is preferably 0.01 or more, more preferably 0.02 or more, even more preferably 0.04 or more, and further preferably 0.07 or more. The mass ratio of the component (b) to the component (a) (b/a) is preferably 0.70 or less, and when the component (b) contains polyvinyl butyral, the ratio is preferably 0.55 or less, more preferably 0.50 or less, even more preferably 0.30 or less, and further preferably 0.25 or less. Specifically, the content mass ratio of the component (b) to the component (a) (b/a) is preferably 0.01 or more and 0.70 or less, more preferably 0.02 or more and 0.70 or less, even more preferably 0.07 or more and 0.70 or less, or is preferably 0.01 or more and 0.55 or less, more preferably 0.02 or more and 0.50 or less, even more preferably 0.04 or more and 0.30 or less, and further preferably 0.07 or more and 0.25 or less.

The liquid composition may contain an additional component together with the component (a), the component (b), and the component (c) described above. Examples of the additional component include a plasticizer for the polymer capable of forming a film as the component (b), a color pigment, an extender pigment, a dye, a surfactant, a UV protective agent, a flavoring agent, a repellent, an antioxidant, a stabilizer, an antiseptic agent, and various vitamins. When the spraying composition contains an additional component, the content of the additional component is preferably 0.1% by mass or more and 30% by mass or less and more preferably 0.5% by mass or more and 20% by mass or less. When the liquid composition contains a powder component having a particle size of 0.1 μm or more at 20° C., such as a color pigment and an extender pigment, the content of the powder component is preferably 1% by mass or less, more preferably 0.5% by mass or less, and even more preferably 0.1% by mass or less from the viewpoint of prevention of nozzle clogging of the electrostatic spray device described later and film adhesion. The composition more preferably contains no powder component.

In particular, when the liquid composition contains the component (c), a salt can be further added as component (d) in view of an improvement in conductivity of the liquid composition and successful film formation by the electrostatic spraying method. In view of an improvement in conductivity, the component (d) is preferably an alkali metal salt or an ammonium salt. In view of a further improvement in dispersibility in the liquid composition containing the component (b) and of a further improvement in conductivity, the component (d) is preferably one or more compounds selected from ionic compounds and acylamino acid esters and more preferably one or more compounds selected from ionic surfactants, ionic polymers, betaine compounds, and acylamino acid esters.

Examples of the ionic surfactant include a cationic surfactant, an anionic surfactant, and an amphoteric surfactant.

The cationic surfactant is preferably a quaternary ammonium salt. The anionic surfactant is preferably an acylamino acid salt. The component (d) is more preferably one or more compounds selected from quaternary ammonium salts and acylamino acid salts.

Examples of the quaternary ammonium salt include a tetraalkylammonium salt, a benzylalkylammonium salt, a benzyltrialkylammonium salt, an alkylbenzyldimethylammonium salt, a mono-long-chain alkyltrimethylammonium salt, and a di-long-chain alkyldimethylammonium salt. Specific examples of the quaternary ammonium salt include cetyltrimethylammonium chloride, stearyltrimethylammonium chloride, behenyltrimethylammonium chloride, behenyldimethylhydroxyethylammonium chloride, distearyldiammonium chloride, stearyldimethylbenzylammonium chloride, distearyldimethylammonium chloride, dicetylmethylammonium chloride, cetyltriethylammonium methylsulfate, and benzalkonium chloride.

Examples of the acylamino acid salt include an acyl glutamate, an acyl aspartate, an acyl sarcosinate, an acyl taurate, and an acyl methyltaurate, and the salt is preferably an alkali metal salt or an ammonium salt. Examples of the acylamino acid salt include sodium myristoyl glutamate, sodium myristoyl aspartate, sodium cocoyl glutamate, sodium lauroyl glutamate, sodium lauroyl aspartate, sodium lauroyl sarcosinate, and sodium palmitoyl sarcosinate.

Examples of the amphoteric surfactant include a betaine surfactant and a sulfobetaine surfactant and specifically include cocamide propyl betaine and cocamide propyl hydroxysultaine.

Examples of the ionic polymer include an anionic polymer, a cationic polymer, and an ampholytic polymer. Examples of the anionic polymer include a homopolymer or copolymer having a (meth)acrylic acid unit, including an acrylate/C1-18 alkyl acrylate/C1-8 alkyl acrylamide copolymer AMP. Examples of the cationic polymer include a homopolymer or copolymer having a primary to tertiary amino group or a quaternary ammonium group, including an ethyl acrylate/N-[3-(dimethylamino)propyl]acrylamide/N-tert-butylacrylamide/methacrylate-α-methyl-poly(oxyethylen)-ω-yl copolymer and a poly(N-propanoylethyleneimine)-grafted-dimethylsiloxane/γ-aminopropylmethylsiloxane copolymer monoethyl sulfate. Examples of the ampholytic polymer include a homopolymer or copolymer having an alkyl betaine unit or a sulfobetaine unit and specifically include an N-methylacryloyloxyethyl-N,N-dimethylammonium-α-N-methylcarboxybetaine/alkyl methacrylate copolymer.

Examples of the betaine compound include an amino acid compound having three methyl groups on an amino group, such as trimethylglycine, carnitine (vitamin Bt; 3-hydroxy-4-(trimethylammonio)butanoate ester), and an acylated carnitine.

Examples of the acylamino acid ester include an acylamino acid (phytosteryl/octyldodecyl) ester and specifically include di(phytosteryl/octyldodecyl) lauroyl glutamate.

In particular, the component (d) is preferably one or more compounds selected from cationic surfactants, anionic surfactants, amphoteric surfactants, acylamino acid esters, anionic polymers, cationic polymers, ampholytic polymers, and betaine compounds, and is more preferably one or more compounds selected from quaternary ammonium salts, acylamino acid salts, acylamino acid ester salts, homopolymers or copolymers having a (meth)acrylic acid unit, homopolymers or copolymers having a primary to tertiary amino group, homopolymers or copolymers having a quaternary ammonium group, homopolymers or copolymers having an alkyl betaine unit or a sulfobetaine unit, and trimethylglycine.

When a salt is further added as the component (d), the content of the component (d) in the liquid composition is preferably 0.01% by mass or more, more preferably 0.05% by mass or more, and even more preferably 0.1% by mass or more and is preferably 10% by mass or less, more preferably 8% by mass or less, even more preferably 6% by mass or less, further preferably 2.5% by mass or less, and furthermore preferably 2% by mass or less, in view of stable formation of a film and prevention of an excess increase in the conductivity described later. Specifically, the content of the component (d) is preferably 0.01% by mass or more and 10% by mass or less, more preferably 0.05% by mass or more and 8% by mass or less, and even more preferably 0.1% by mass or more and 6% by mass or less.

In view of film formability and an improvement in spinning stability, the mass ratio of the content of the component (d) to that of the component (c), d/c, is preferably 0.01 or more, more preferably 0.02 or more, and even more preferably 0.03 or more and is preferably 6 or less, more preferably 5 or less, and even more preferably 4 or less. Specifically, the mass ratio of the content of the component (d) to the component (c), d/c, is preferably 0.01 or more and 6 or less, more preferably 0.02 or more and 5 or less, and even more preferably 0.03 or more and 4 or less.

The liquid composition used in the electrostatic spraying method preferably has a viscosity at 25° C. of 5 mPa·s or more, more preferably 10 mPa·s or more, even more preferably 20 mPa·s or more, and further preferably 30 mPa·s or more. The liquid composition used preferably has a viscosity at 25° C. of 3,000 mPa·s or less, more preferably 2,000 mPa·s or less, even more preferably 1,500 mPa·s or less, further preferably 1,000 mPa·s or less, and furthermore preferably 800 mPa·s or less. The liquid composition preferably has a viscosity at 25° C. of 5 mPa·s or more and 3,000 mPa·s or less, more preferably 5 mPa·s or more and 2,000 mPa·s or less, even more preferably 10 mPa·s or more and 1,500 mPa·s or less, preferably 20 mPa·s or more and 1,000 mPa·s or less, and furthermore preferably 30 mPa·s or more and 800 mPa·s or less. By using a liquid composition having a viscosity within the range, a porous film, especially a porous film including deposited fibers can be successfully formed by the electrostatic spraying method. The formation of a porous film is advantageous from the viewpoint of following performance to skin, prevention of humid skin, or the like. The viscosity of a liquid composition is determined by using an E-type viscometer at 25° C. As the E-type viscometer, for example, an E-type viscometer manufactured by Tokyo Keiki Inc. can be used. The measurement is performed in conditions at 25° C. with a cone plate rotor No. 43, and the rotation rate is appropriately selected depending on a viscosity: 5 rpm for a viscosity of 500 mPa·s or more; 10 rpm for a viscosity of not less than 150 mPa·s and less than 500 mPa·s; and 20 rpm for a viscosity of less than 250 mPa·s.

From the viewpoint of stable formation of a film on skin, the liquid composition for the electrostatic spraying method preferably has a conductivity at 25° C. of 8 µS/cm or more, more preferably 10 µS/cm or more, even more preferably 20 µS/cm or more, and further preferably 25 µS/cm or more. From the same viewpoint, the liquid composition preferably has a conductivity of 300 µS/cm or less, more preferably 260 µS/cm or less, even more preferably 220 µS/cm or less, and further preferably 200 µS/cm or less. More specifically, the liquid composition preferably has a conductivity at 25° C. of 8 µS/cm or more and 300 µS/cm or less, more preferably 8 µS/cm or more and 260 µS/cm or less, even more preferably 10 µS/cm or more and 260 µS/cm or less, further preferably 10 µS/cm or more and 220 µS/cm or less, and furthermore preferably 25 µS/cm or more and 200 µS/cm or less. The conductivity of a liquid composition can be determined by using an impedance analyzer (S11260, manufactured by Solartron) with a measurement terminal (SH-Z), in conditions of 25° C., φ10 mm, and a distance of 1 mm. The conductivity of the liquid composition at 25° C. can be appropriately adjusted by changing the mixing ratios of the component (a), the component (b), the component (c), and/or the component (d), provided that the above mixing ranges of the components are satisfied.

In the liquid composition, the ratio of the conductivity Y (S/cm) to the viscosity X (mPa·s) at 25° C., Y/X, is preferably 0.1 or more, more preferably 0.2 or more, and even more preferably 0.3 or more and is preferably 3.3 or less, more preferably 3 or less, even more preferably 2.5 or less, and further preferably 2 or less, in view of stable formation of a fibrous film and an improvement in adhesion of a film. Specifically, the ratio of the conductivity Y (µS/cm) to the viscosity X (mPa·s) at 25° C., Y/X, is preferably 0.1 or more and 3.3 or less, more preferably 0.2 or more and 3 or less, and even more preferably 0.3 or more and 2.5 or less.

The liquid composition is sprayed by the electrostatic spraying method directly on an application site of human skin as an object. The electrostatic spraying method includes the step of electrostatically spraying a liquid composition on the skin surface using an electrostatic spray device. FIG. 1 is a schematic view showing the configuration of an electrostatic spray device suitably used in the present invention. An electrostatic spray device 10 shown in the figure includes a low-voltage power supply 11. The low-voltage power supply 11 can generate voltages at several volts to ten-odd volts. In order to improve the portability of the electrostatic spray device 10, the low-voltage power supply 11 preferably includes one or more batteries. Using batteries as the low-voltage power supply 11 also provides an advantage such that batteries can be easily replaced as needed. In place of batteries, an AC adapter or the like can also be used as the low-voltage power supply 11.

The electrostatic spray device 10 also includes a high-voltage power supply 12. The high-voltage power supply 12 is connected to the low-voltage power supply 11 and includes an electric circuit (not shown) for boosting the voltage generated by the low-voltage power supply 11 to a high voltage. The booster circuit typically includes a transformer, a capacitor, a semiconductor device, and the like.

The electrostatic spray device 10 further includes an auxiliary circuit 13. The auxiliary circuit 13 is located between the low-voltage power supply 11 and the high-voltage power supply 12 and functions to control the voltage of the low-voltage power supply 11 for stable operation of the high-voltage power supply 12. The auxiliary circuit 13 also functions to control the rotation rate of a motor included in the microgear pump 15A described later. By controlling the rotation rate of the motor, the amount of a liquid composition fed from the liquid composition container 14 described later to the microgear pump 15A is controlled. Between the auxiliary circuit 13 and the low-voltage power supply 11, a switch SW is provided, and on/off control of the switch SW enables operation/stop of the electrostatic spray device 10.

The electrostatic spray device 10 further includes a nozzle 15. The nozzle 15 is made from various conductors including metal or non-conductors including plastic, rubber, and ceramic and has a shape capable of ejecting a liquid composition from the tip thereof. In the nozzle 15, a microspace through which a liquid composition passes is formed along the longitudinal direction of the nozzle 15. From the viewpoint of preventing the nozzle 15 from clogging, the microspace preferably has a minimum cross-sectional diameter of 100 µm or more and 2,000 µm or less, more preferably 100 µm or more and 1,400 µm or less, even more preferably 250 µm or more and 1,400 µm or less, and further preferably 300 µm or more and 1,400 µm or less. From the same viewpoint, the nozzle 15 preferably has a flow path length of 1 mm or more and 25 mm or less, more preferably 1 mm or more and 20 mm or less, even more preferably 5 mm or more and 20 mm or less, and further preferably 5 mm or more and 15 mm or less.

The flow path of the nozzle 15 can have at least a tubular shape, and the flow path may branch at a midway point as long as a liquid composition can be ejected. As for the cross section of the flow path, the flow path may have a cylinder shape (tube shape) having a substantially constant cross-sectional area, or the cross-sectional area of a flow path may increase or decrease toward the ejecting direction of a liquid composition.

The nozzle 15 communicates through a pipeline 15B with the microgear pump 15A. The pipeline 15B may be conductive or non-conductive. The nozzle 15 is electrically connected to the high-voltage power supply 12. This structure enables high voltage application to the nozzle 15. In this case, in order to prevent an excess current from flowing when a human body comes into direct contact with the nozzle 15, the nozzle 15 and the high-voltage power supply 12 are electrically connected through a current-limiting resistor 19. The nozzle 15 and the high-voltage power supply 12 may be electrically connected through an electric conductor (not shown) such as an electrode.

The microgear pump 15A communicating through the pipeline 15B with the nozzle 15 functions as a feeder for feeding a liquid composition stored in the container 14 to the nozzle 15. The microgear pump 15A is activated in response to power supply from the low-voltage power supply 11. The microgear pump 15A is so constructed as to feed a certain amount of the liquid composition to the nozzle 15 in response to control by the auxiliary circuit 13.

To the microgear pump 15A, the container 14 is connected through a flexible pipeline 15C. In the container 14, a liquid composition is stored. The container 14 preferably has a replaceable cartridge shape.

The flow rate of a liquid composition ejected from the nozzle 15 depends on the formulation of a liquid composition or an application site on skin and is preferably 0.1 mL/h or more, more preferably 0.2 mL/h or more, and even more preferably 0.4 mL/h or more. The flow rate of a liquid composition ejected from the nozzle 15 is preferably 100 mL/h or less, more preferably 50 mL/h or less, even more preferably 30 mL/h or less, further preferably 12 mL/h or less, and furthermore preferably 11.5 mL/h or less. More specifically, the flow rate of a liquid composition ejected from the nozzle 15 is preferably 0.1 mL/h or more and 100 mL/h or less, more preferably 0.2 mL/h or more and 50 mL/h or less, even more preferably 0.4 mL/h or more and 30 mL/h or less, further preferably 0.4 mL/h or more and 12 mL/h or less, and furthermore preferably 0.4 mL/h or more and 11.5 mL/h or less. By ejecting a liquid composition at the flow rate, the film formability can be improved, and the adhesion of a film to skin can be improved.

The voltage applied by the high-voltage power supply 12 to the nozzle 15 is preferably 5 kV or more, more preferably 9 kV or more, and even more preferably 10 kV or more from the viewpoint of maintaining the ejection flow rate of a liquid composition in the electrostatic spraying step. The voltage applied to the nozzle 15 is preferably 50 kV or less and more preferably 30 kV or less. More specifically, the voltage applied to the nozzle 15 is preferably 5 kV or more and 50 kV or less, more preferably 9 kV or more and 30 kV or less, and even more preferably 10 kV or more and 30 kV or less. The voltage applied to the nozzle 15 can be appropriately set depending on the formulation of a liquid composition or an intended ejecting rate of a liquid composition, and a higher voltage is preferably applied as the flow rate increases. The voltage range applied to the nozzle 15 is an absolute value, and the applied voltage may be a positive voltage or a negative voltage based on grounding.

When the liquid composition contains the component (c), the ejecting rate (flow rate F) of a liquid composition from the nozzle 15 and the voltage P applied to the nozzle 15 preferably satisfy a particular relation, provided that the flow rate and the voltage are within the above ranges, from the viewpoint of successful electrostatic spraying and a further improvement in adhesion of a film to skin or the like. The ratio of the ejecting rate F (flow rate: mL/h) of a liquid composition to the voltage P (kV) applied to the nozzle 15 (flow rate/voltage) is preferably 0.8 or less and more preferably 0.6 or less, and the lower limit is preferably 0.06 or more and more preferably 0.1 or more, provided that the flow rate and the voltage satisfy the above ranges. In the above condition, the flow rate is preferably 0.2 mL/h or more, more preferably 0.4 mL/h or more, even more preferably 1 mL/h or more, and further preferably 2 mL/h or more.

In particular, when a hand-held electrostatic spray device is used to perform electrostatic spraying directly on skin, ambient environment including humidity may vary or the distance between the nozzle held by a person and skin may vary at the time of electrostatic spraying. From the viewpoint of achieving film formability on skin independent of such variation factors, the relation between the voltage P (kV) applied to the nozzle 15 and the flow rate F (mL/h) is preferably $(1 \leq F \leq 0.6P)$, more preferably $(1 \leq F \leq 0.5P+2)$, even more preferably $(1 \leq F \leq 0.3P+2.5)$, further preferably $(2 \leq F \leq 0.5P+2)$, and furthermore preferably $(2 \leq F \leq 0.3P+2.5)$. Such mathematical expressions can be supported by Examples described later.

From the viewpoint of satisfying both the handling properties of the electrostatic spray device 10 and satisfactory ejection of a liquid composition, the container 14 preferably has a volume of 1 mL or more, more preferably 1.5 mL or more, and even more preferably 3 mL or more and is preferably 25 mL or less, more preferably 20 mL or less, and even more preferably 15 mL or less. Specifically, the container 14 preferably has a volume of 1 mL or more and 25 mL or less, more preferably 1.5 mL or more and 20 mL or less, and even more preferably 3 mL or more and 15 mL or less. The container 14 having a volume within such a range also has an advantage that such a compact container can be easily replaced when the container 14 is a replaceable cartridge.

Other embodiments of the electrostatic spray device used in the present invention will next be described with reference to FIG. 2 to FIG. 6. The electrostatic spray devices 10 shown in FIG. 2 to FIG. 6 differ from the electrostatic spray device shown in FIG. 1 in that a cartridge and a main body are included. For the embodiments shown in FIG. 2 to FIG. 6, the explanation of the embodiment shown in FIG. 1 will be appropriately applied unless otherwise specified. In FIG. 2 to FIG. 6, the same members as in FIG. 1 are indicated by the same signs.

Figure 2:
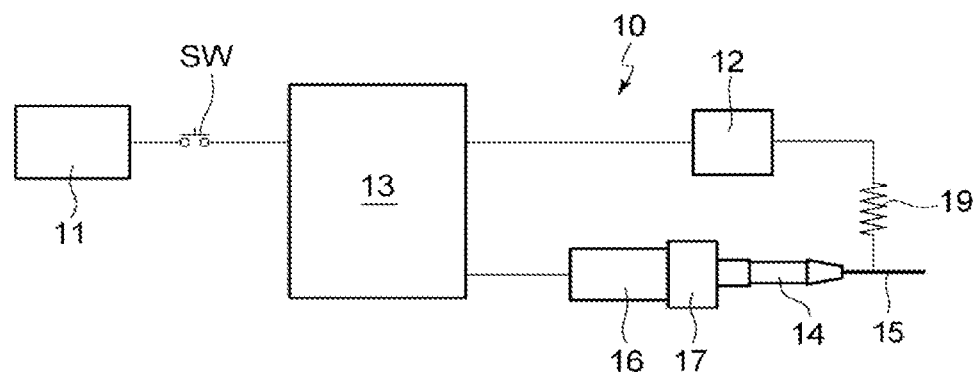
FIG. 2 is a schematic view showing the configuration of another embodiment of the electrostatic spray device used in the present invention.
Figure 3:
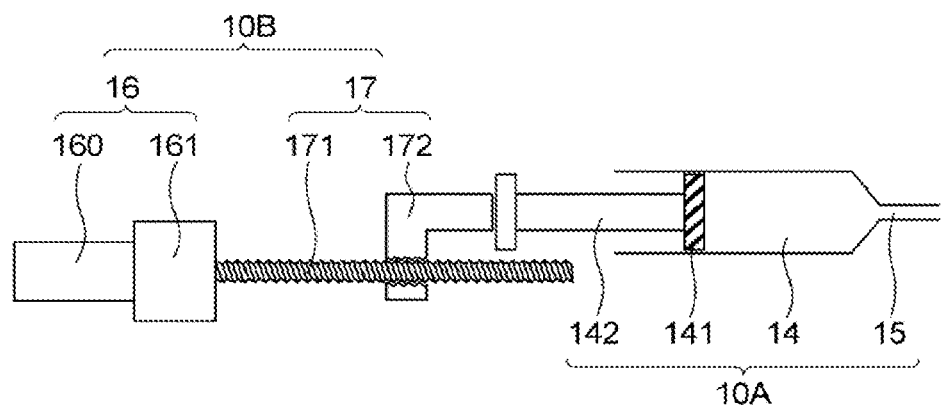
FIG. 3 is a schematic view showing the structure of a cartridge and a main body included in the electrostatic spray device shown in FIG. 2.
Figure 4:
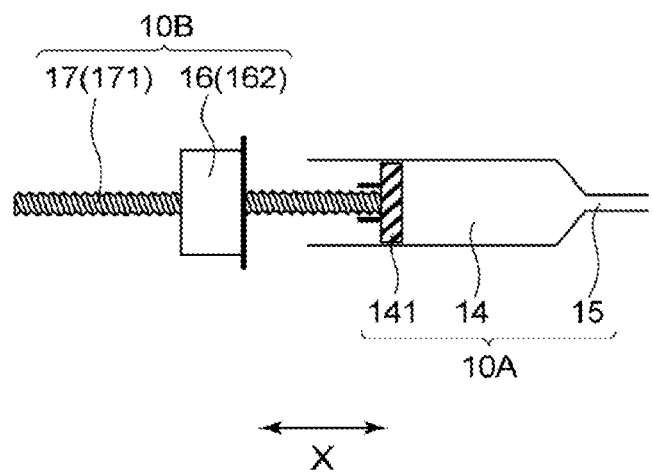
FIG. 4 is a schematic view showing another embodiment of the cartridge and the main body included in the electrostatic spray device shown in FIG. 2.

An electrostatic spray device 10 of the embodiment shown in FIG. 2 or FIG. 3 includes a cartridge 10A and a main body 10B as main components. The cartridge 10A includes a container 14, a gasket 141, a plunger 142, and a nozzle 15. The main body 10B includes a low-voltage power supply 11, a high-voltage power supply 12, an auxiliary circuit 13, a power source 16 including a direct current motor 160 and a motor speed reducer 161, and a power transmitter 17 including a screw shaft 171 and a feed screw 172.

The cartridge 10A is detachable from the main body 10B. With this structure, the electrostatic spray device 10 of the present embodiment can facilitate refilling of a liquid composition and can keep the nozzle 15 clean. Examples of the detachable manner of the cartridge 10A from the main body 10B include, but are not limited to, a method of forming fitting portions on the plunger 142 and the feed screw 172 to fit together and a method of forming screw threads on the plunger 142 and the feed screw 172 to screw together.

As shown in FIG. 3, the cartridge 10A includes a cylinder-shaped container 14 capable of storing a liquid composition. The container 14 has an opening at one end. The container 14 has the nozzle 15 at the other end. The container 14 includes the gasket 141 therein. The gasket 141 has the same outline shape as the cross-sectional shape of the container 14. With this shape, the gasket 141 is slidable in the container 14 while being in fluid-tight contact with the inner surface of the container 14. The gasket 141 is bonded to the front end of the plunger 142. The plunger 142 extends outward from the container 14 over the opening of the container 14. The plunger 142 engages at the rear end with the feed screw 172. The container 14 may be conductive or non-conductive.

The nozzle 15 in the present embodiment communicates with the container 14. The nozzle 15 is electrically connected to the high-voltage power supply 12. This structure enables high voltage application to the nozzle 15. In this case, in order to prevent an excess current from flowing when a human body comes into direct contact with the nozzle 15, the nozzle 15 and the high-voltage power supply 12 are electrically connected through a current-limiting resistor 19. The nozzle 15 and the high-voltage power supply 12 may be electrically connected through an electric conductor (not shown) such as an electrode.

Hereinbefore, the cartridge 10A in the electrostatic spray device 10 of the present embodiment has been described, and the main body 10B of the embodiment will next be described.

The main body 10B includes the low-voltage power supply 11. The low-voltage power supply 11 can generate voltages at several volts to ten-odd volts. In order to improve the portability of the electrostatic spray device 10, the low-voltage power supply 11 preferably includes one or two or more batteries. Using batteries as the low-voltage power supply 11 also provides such an advantage that batteries can be easily replaced as needed. In place of batteries, an AC adapter or the like can also be used as the low-voltage power supply 11.

The main body 10B further includes the high-voltage power supply 12. The high-voltage power supply 12 is connected to the low-voltage power supply 11 and includes an electric circuit (not shown) for boosting the voltage generated by the low-voltage power supply 11 to a high voltage. The booster circuit typically includes a transformer, a capacitor, a semiconductor device, and the like.

The main body 10B further includes the auxiliary circuit 13. The auxiliary circuit 13 is located between the low-voltage power supply 11 and the high-voltage power supply 12 and functions to control the voltage of the low-voltage power supply 11 for stable operation of the high-voltage power supply 12. The auxiliary circuit 13 also functions to control the rotation rate of a motor included in the power source 16 described later. By controlling the rotation rate of the motor, the amount of a liquid composition fed from the container 14 storing the liquid composition to the nozzle 15 ejecting the liquid composition is controlled. Between the auxiliary circuit 13 and the low-voltage power supply 11, a switch SW is provided, and on/off control of the switch SW enables operation/stop of the electrostatic spray device 10.

The main body 10B further includes the power source 16 and the power transmitter 17. The power source 16 generates a motive power to eject a liquid composition stored in the container 14 from the nozzle 15. The power source 16 receives power supply from the low-voltage power supply 11 and is activated in response to control by the auxiliary circuit 13. The device is so constructed that the power source 16 generates a motive power that is transmitted through the power transmitter 17 to the cartridge 10A and to feed a certain amount of a liquid composition from the container 14 to the nozzle 15.

The main body 10B includes the power source 16 including the direct current motor 160 and the motor speed reducer 161 and the power transmitter 17 including the screw shaft 171 and the feed screw 172.

The direct current motor 160 is connected to the motor speed reducer 161 that reduces the rotation power of the direct current motor 160 and outputs the power. The motor speed reducer 161 is connected to the rotatable screw shaft 171. The direct current motor 160 generates a rotation power that is transmitted through the motor speed reducer 161 to the screw shaft 171, and the screw shaft 171 is rotated. The rotation power transmitted to the screw shaft 171 is converted by the feed screw 172 connected to the screw shaft 171 into a linear motive power that carries the feed screw 172 along the longitudinal direction X. The linearly moving feed screw 172 pushes the plunger 142 and the gasket 141 into the container 14, and this allows a liquid composition stored in the container 14 to be sprayed through the nozzle 15 to the outside.

In FIG. 3, the feed screw 172 is separated from the plunger 142, and the plunger 142 and the gasket 141 are integrated. A feed screw 172 and a plunger 142 may be integrated, and a plunger 142 may be separated from a gasket 141, or a feed screw 172 may be in direct contact with a gasket 141 to transmit a linear motive power to the gasket 141.

Due to electric conductivity of a liquid composition used in the present invention, a high voltage applied to the nozzle 15 may be applied through the liquid composition stored in the container 14 or the power transmitter 17 to the power source 16, and the electrostatic spray device 10 may be damaged, or charges may leak to result in spray failure. Hence, from the viewpoint of ensuring the insulating properties to prevent damages to the electrostatic spray device 10 when the electrostatic spray device 10 is used and of preventing current leakage through a liquid composition to ensure spinning stability, the power transmitter 17 preferably electrically insulates the power source 16 from the cartridge 10A. This structure can effectively prevent a high voltage applied to the nozzle 15 from being applied to the power source 16 unintentionally. Examples of the method of electrically insulating the power source 16 from the cartridge 10A include a method of using a screw shaft 171 or a feed screw 172 formed from a non-conductive material such as plastic and ceramic as the power transmitter 17. When the power transmitter 17 electrically insulates the power source 16 from the cartridge 10A, the gasket 141 or the plunger 142 may be conductive or non-conductive.

FIG. 4 shows another embodiment of the electrostatic spray device 10 suitably used in the present invention. For the embodiment shown in FIG. 4, the explanation of the embodiment shown in FIG. 2 or FIG. 3 will be appropriately applied unless otherwise specified. In FIG. 4, the same members as in FIG. 2 or FIG. 3 are indicated by the same signs.

As shown in FIG. 4, a cartridge 10A includes a container 14, a gasket 141, and a nozzle 15. A main body 10B includes a power source 16 including a linear stepping motor 162 and a power transmitter 17 including a screw shaft 171. With these structures, the amount of a liquid composition fed from the container 14 to the nozzle 15 can be precisely controlled, and the electrostatic spray device 10 can have a higher portability due to the compact main body 10B.

The linear stepping motor 162 includes a rotor (not shown) having a female screw therein. The female screw of the rotor screws the screw shaft 171 as a male screw. The linear stepping motor 162 is fixed to a frame (not shown) of the main body 10B. By rotation of the rotor in the linear stepping motor 162, the screw shaft 171 screwed by the female screw of the rotor moves linearly along the longitudinal direction X. The linearly moving screw shaft 171 pushes the gasket 141, which is in contact with one end of the screw shaft 171, into the container 14, and this allows a liquid composition stored in the container 14 to be sprayed through the nozzle 15 to the outside.

FIG. 5 shows another embodiment of the electrostatic spray device. An electrostatic spray device 10 shown in the figure includes a cartridge 10A and a main body 10B as main components. The cartridge 10A includes a container 14, a nozzle 15, and a pump 15P. The main body 10B includes a low-voltage power supply 11, a high-voltage power supply 12, an auxiliary circuit 13, a power source 16, and a power transmitter 17.

The cartridge 10A is detachable from the main body 10B. With this structure, the electrostatic spray device 10 of the present embodiment can facilitate refilling of a liquid composition and can keep the nozzle 15 clean. Examples of the detachable manner of the cartridge 10A from the main body 10B include, but are not limited to, a method of forming a fitting portion on the power transmitter 17 described later to fit the pump 15P and the power source 16 together through the power transmitter 17.

The container 14 can store a liquid composition and is detachable from the cartridge 10A. With this structure, the electrostatic spray device 10 of the present embodiment can facilitate refilling of a liquid composition. Examples of the detachable manner of the container 14 from the cartridge 10A include, but are not limited to, a method of forming fitting portions on the container 14 and the pump 15P to fit together.

Figure 6:
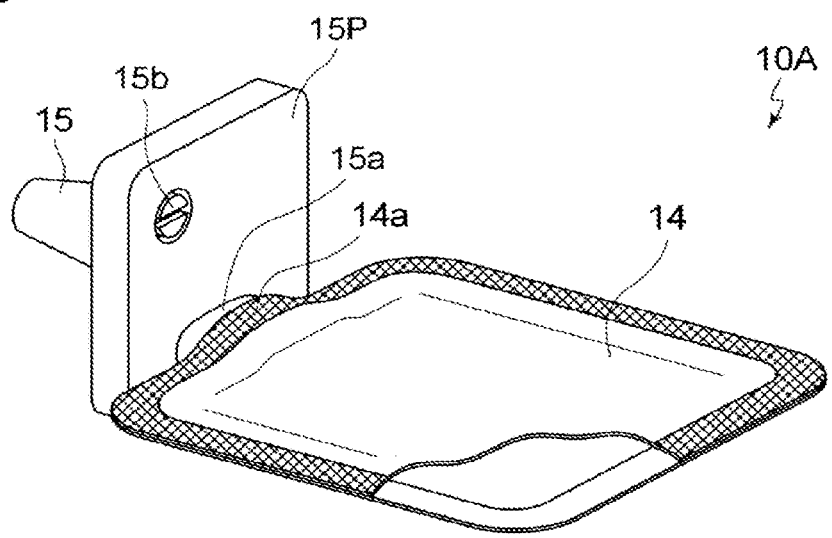
FIG. 6 is a schematic view showing the structure of a cartridge included in the electrostatic spray device shown in FIG. 5.

FIG. 6 shows the cartridge 10A in the present embodiment. The cartridge 10A includes a bag-like container 14. The container 14 is formed as follows: two sheets made from a liquid impermeable, flexible material such as polyethylene are stacked; and the outer edges thereof are fluid-tightly joined into a flat bag. The container 14 accordingly has a deformable structure, and a liquid composition can be stored in the container 14. The container 14 has, on a part of the outer edge thereof, an opening 14a capable of communicating with the pump 15P for feeding a liquid composition to the pump 15P. The container 14 may be conductive or non-conductive.

The nozzle 15 in the present embodiment communicates with the pump 15P. The nozzle 15 is electrically connected to the high-voltage power supply 12. This structure enables high voltage application to the nozzle 15. In this case, in order to prevent an excess current from flowing when a human body comes into direct contact with the nozzle 15, the nozzle 15 and the high-voltage power supply 12 are electrically connected through a current-limiting resistor 19. The nozzle 15 and the high-voltage power supply 12 may be electrically connected through an electric conductor (not shown) such as an electrode. The nozzle 15 may further have a pipeline for communication with the pump 15P. The pipeline may be conductive or non-conductive.

The cartridge 10A includes the pump 15P. The pump 15P is located between the container 14 and the nozzle 15 and communicates with them. The pump 15P has a connector 15a for connection with the opening 14a of the container 14. With this structure, a liquid composition stored in the container 14 can be fed to the nozzle 15 while fluid-tightness of the flow path between the container 14 and the pump 15P is maintained. The pump 15P is driven in response to the transmission of a motive power from the power source 16 described later through the power transmitter 17. The pump 15P shown in FIG. 6 further includes a rotatable power transmission depression 15b for transmitting the motive power from the power source 16 through the power transmitter 17 to an internal mechanism (not shown) such as a gear in the pump 15P. As the pump 15P, a gear pump or the like is used from the viewpoint of an improvement in constant ejection amount of a liquid composition and an improvement in portability of the electrostatic spray device 10. As the gear pump, for example, the microgear pump described in the embodiment shown in FIG. 1 can be used.

When the pump 15P is activated to feed a liquid composition from the container 14 to the nozzle 15, the amount of the liquid composition in the container 14 is reduced as the composition is fed to the nozzle 15, and the internal pressure of the container 14 decreases due to fluid-tightness of the flow path between the container 14 and the pump 15P. Accordingly, the container 14 made from a flexible, deformable material deforms to flatten in proportion to the internal pressure.

Hereinbefore, the cartridge 10A in the electrostatic spray device 10 of the present embodiment has been described, and the main body 10B of the embodiment will next be described.

The main body 10B includes the low-voltage power supply 11. The low-voltage power supply 11 can generate voltages at several volts to ten-odd volts. In order to improve the portability of the electrostatic spray device 10, the low-voltage power supply 11 preferably includes one or two or more batteries. Using batteries as the low-voltage power supply 11 also provides such an advantage that batteries can be easily replaced as needed. In place of batteries, an AC adapter or the like can also be used as the low-voltage power supply 11.

The main body 10B includes the high-voltage power supply 12. The high-voltage power supply 12 is connected to the low-voltage power supply 11 and includes an electric circuit (not shown) for boosting the voltage generated by the low-voltage power supply 11 to a high voltage. The booster circuit typically includes a transformer, a capacitor, a semiconductor device, and the like.

The main body 10B includes the auxiliary circuit 13. The auxiliary circuit 13 is located between the low-voltage power supply 11 and the high-voltage power supply 12 and functions to control the voltage of the low-voltage power supply 11 for stable operation of the high-voltage power supply 12. The auxiliary circuit 13 also functions to control the rotation rate of a motor included in the power source 16 described later. By controlling the rotation rate of the motor, the amount of a liquid composition fed from the container 14 storing the liquid composition through the pump 15P to the nozzle 15 ejecting the liquid composition is controlled. Between the auxiliary circuit 13 and the low-voltage power supply 11, a switch SW is provided, and on/off control of the switch SW enables operation/stop of the electrostatic spray device 10.

The main body 10B further includes the power source 16 and the power transmitter 17. The power source 17 of the present embodiment generates a motive power to eject a liquid composition stored in the container 14 through the pump 15P from the nozzle 15. The power source 16 in the present invention includes a motor and the like, receives power supply from the low-voltage power supply 11, and is activated in response to control by the auxiliary circuit 13 to generate a motive power. The device is so constructed that the power source 16 generates a motive power that is transmitted through the power transmitter 17 to the pump 15P and to feed a certain amount of a liquid composition from the container 14 through the pump 15P to the nozzle 15.

The power transmitter 17 included in the main body 10B transmits a motive power generated by the power source 16 such as a motor to the pump 15P. Accordingly, a liquid composition stored in the container 14 can be fed through the pump 15P to the nozzle 15. The method of transmitting a motive power from the power source 16 to the pump 15P is not necessarily limited. For example, a projection structure (not shown) is formed at a tip of the power transmitter 17 as a shaft, then the projection structure is fitted with the power transmission depression 15b formed on the pump 15P, and the rotation power of a motor in the power source 16 can be transmitted to the pump 15P.

Due to electric conductivity of a liquid composition used in the present invention, a high voltage applied to the nozzle 15 may be applied through the pump 15P or the power transmitter 17 to the power source 16, and the electrostatic spray device 10 may be damaged, or charges may leak to result in spray failure. Hence, from the viewpoint of ensuring the insulating properties to prevent damages to the electrostatic spray device 10 when the electrostatic spray device 10 is used and of preventing current leakage through a liquid composition to ensure spinning stability, the power transmitter 17 preferably electrically insulates the power source 16 from the cartridge 10A. This structure can effectively prevent a high voltage applied to the nozzle 15 from being applied to the power source 16 unintentionally. Examples of the method of electrically insulating the power source 16 from the cartridge 10A include a method of using, as the power transmitter 17, a member formed from a non-conductive material such as plastic and ceramic. When the power transmitter 17 electrically insulates the power source 16 from the cartridge 10A, other constituent materials may be conductive or non-conductive.

With the above structure, the amount of a liquid composition fed from the container 14 to the nozzle 15 can be precisely controlled, and the electrostatic spray device 10 can have a higher portability due to the compact main body 10B.

Figure 7:
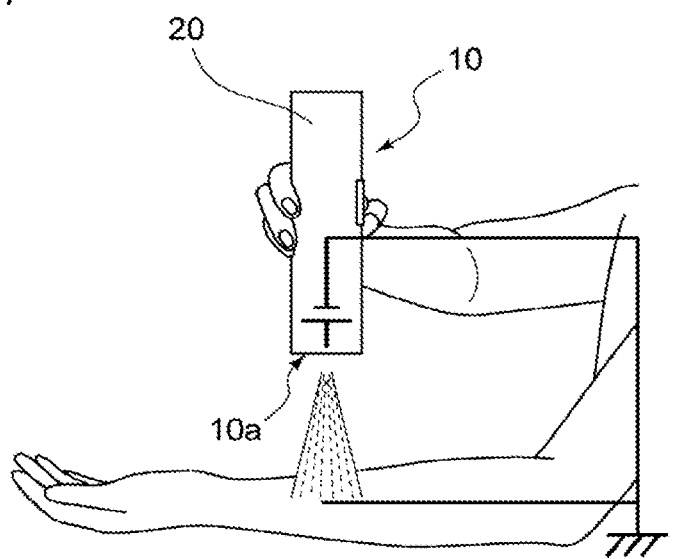
FIG. 7 is a schematic view showing a state in which an electrostatic spray device is used to perform an electrostatic spraying method.

The electrostatic spray devices 10 having the configurations in the embodiments shown in FIG. 1 to FIG. 6 can be used as shown in FIG. 7, for example. FIG. 7 shows a hand-held electrostatic spray device 10 having dimensions that allow a user to hold the device with one hand. The electrostatic spray device 10 shown in the figure stores all the members in the configuration views shown in FIG. 1, FIG. 2, or FIG. 5 in a cylindrical housing 20. The housing 20 shown in FIG. 7 has a cylindrical shape, but a housing 20 may have any shape as long as the housing has dimensions that allows a user to hold the device with one hand, and all the constituent members shown in FIG. 1 are stored. The shape may be an elliptical tube or a regular prism. For the "dimensions that allow a user to hold a device with one hand", the housing 20 containing the electrostatic spray device 10 preferably has a weight of 2 kg or less, the housing 20 preferably has a maximum length of 40 cm or less in the longitudinal direction, and the housing 20 preferably has a volume of 3,000 cm$^3$ or less. The housing 20 has a nozzle (not shown) at one end 10a in the longitudinal direction. The nozzle is so provided on the housing 20 as to form a convex toward skin while the ejection direction of a liquid composition is coincident with the longitudinal direction of the housing 20. When a nozzle tip is provided to form a convex toward skin in the longitudinal direction of the housing 20, a liquid composition is unlikely to adhere to the housing, and a film can be stably formed.

When the electrostatic spray device 10 is operated, a user or a person forming a film on an application site thereof by electrostatic spraying holds the apparatus 10 by hand and directs the one end 10a with the nozzle (not shown) of the apparatus 10 to the application site where electrostatic spraying is to be performed. FIG. 7 shows the state in which the one end 10a of the electrostatic spray device 10 is directed to the inner face of a forearm of a user. In this condition, the apparatus 10 is switched on to perform the electrostatic spraying method. When the apparatus 10 is powered, an electric field is formed between the nozzle and the skin. In the embodiment shown in FIG. 7, a positive high voltage is applied to the nozzle, and the skin functions as a negative electrode. When an electric field is formed between the nozzle and the skin, a liquid composition at the nozzle tip is polarized by electrostatic induction to form a cone-shaped tip, and liquid drops of the charged liquid composition are ejected from the cone tip along the electric field into the air (into the atmosphere) toward the skin. When the component (a) or the component (a) and the component (c) as solvents evaporate from the charged liquid composition ejected into the space, the liquid composition surface has an excess charge density. By Coulomb repulsion, the liquid composition spreads in the space while miniaturized repeatedly, and reaches the skin. In this case, by appropriately adjusting the viscosity of the liquid composition, the sprayed composition in a liquid drop state can reach the application site. Alternatively, during ejection into the space, a volatile substance as the solvent is volatilized from liquid drops, and a polymer capable of forming a film as the solute is solidified. Concurrently, fibers are formed while extended and deformed by a potential difference, and the fibers can be deposited on an application site. For example, a liquid composition having a higher viscosity is likely to be deposited in a fiber shape on an application site. Accordingly, a porous film including deposited fibers is formed on the surface of an application site. A porous film including deposited fibers can also be formed by adjusting the distance between the nozzle and skin or the voltage applied to the nozzle.

During performing the electrostatic spraying method, a high potential difference is formed between the nozzle and skin. However, the impedance is very large, and thus an extremely small current flows through a human body. For example, the inventors of the present invention have ascertained that the current flowing through a human body during performing the electrostatic spraying method is several digits smaller than the current flowing through a human body by static electricity generated in a normal life.

When deposited fibers are formed by the electrostatic spraying method, the fibers preferably have a thickness of 10 nm or more and more preferably 50 nm or more in terms of circle equivalent diameter. The thickness is preferably 3,000 nm or less and more preferably 1,000 nm or less. The fiber thickness can be determined as follows: fibers are observed under, for example, a scanning electron microscope (SEM) at a magnification of 10,000; in the two-dimensional image, ten fibers are arbitrarily selected except defects (fiber aggregates, fiber intersections, and liquid drops); and a line orthogonal to the longitudinal direction of each fiber is drawn; and the thickness of the fiber is measured directly.

Each fiber is a continuous fiber with unlimited length in production principle but preferably has a length at least 100 times larger than the thickness of the fiber. Herein, a fiber having a length at least 100 times larger than the thickness of the fiber is defined as a "continuous fiber". The film produced by the electrostatic spraying method is preferably a discontinuous porous film formed of deposited continuous fibers. The film in such a form can be handled as a single aggregate sheet, and advantageously, the film also has very soft characteristics so that the film is unlikely to fragment even when a shear force is applied thereto and has an excellent following performance to body movement. The film has another advantage of excellent diffusion properties of sweat from skin. The film also has an advantage of easy release of the film. In contrast, a continuous film without pores is difficult to release, and has very poor diffusion properties of sweat so that the film is likely to cause humid skin.

The liquid composition in a fibrous form reaches an application site while maintaining a charged state. As described above, the skin is also charged, and thus the fibers come into close contact with the application site by static electricity. The skin surface has a fine unevenness including skin texture, and thus the fibers come into closer contact with the surface of an application site due to the anchor effect of the unevenness. After the electrostatic spraying is completed as above, the electrostatic spray device 10 is powered off. Accordingly, the electric field between the nozzle and the skin disappears, and the charge on the skin surface is fixed. As a result, the adhesion of the film is further exhibited.

As described above, a liquid composition in a charged state is sprayed from the nozzle tip of the electrostatic spray device into the air (into the atmosphere). When the ambient humidity is high during electrostatic spraying, charges leak due to water in the atmosphere, and a lower voltage than the set value is applied to the nozzle in practice. Accordingly, the liquid composition may be charged at a lower degree and may be insufficiently sprayed. In the techniques disclosed in Patent Literatures 1 and 2, specifically, a composition is ejected, and liquid drops are deposited to form a film; in contrast, in the present invention, continuous fibers are formed by Coulomb repulsion of the liquid composition, and the fibers are deposited to form a film. Hence, if the voltage applied to the nozzle and charges of the liquid composition are reduced in the present invention, the quality of the formed film may be affected. When the liquid composition contains the component (c), the electrostatic spraying can be unlikely to be affected by humidity.

When containing the component (c), the liquid composition of the present invention allows a film to be formed to support water while suppressing the effect of humidity on spraying. Specifically, when the liquid composition contains about 0.2% by mass or more of the component (c) and has a mass ratio of the component (b) to the component (c), b/c, of 0.4 or more, the adhesion between skin and a film is improved, and the film is likely to be transparent, resulting in a more natural appearance. The adhesion is further improved by performing the liquid agent-applying step described later before or after the electrostatic spraying step.

In the industrial production where the environmental conditions for the film production including temperature and humidity are controlled, the production environment varies in a small range. In contrast, the temperature and humidity of the environment where the hand-held electrostatic spray device of the embodiment is used is likely to vary, and accordingly a film is difficult to be stably formed, which is a problem specific to hand-held devices. A liquid composition containing the component (d) in addition to the component (c) has a higher conductivity, and accordingly the liquid composition can be stably sprayed by the electrostatic spray device of the present invention even when the environmental conditions for the film production varies. Hence, a film having high adhesion to skin can be formed.

Hereinbefore, the porous film formed of deposited fibers has been described as an exemplary film, but the film form is not limited to this. A continuous film without pores may be formed, or a porous film not in the form of deposited fibers, for example, a porous film obtained by forming a plurality of through-holes irregularly or regularly formed in a continuous film, that is, a discontinuous film may be formed. As described above, by controlling the viscosity of a liquid composition, the distance between the nozzle and skin, the voltage applied to the nozzle, or other conditions, a film having an intended form can be formed.

The distance between the nozzle and skin depends on the voltage applied to the nozzle and is preferably 10 mm or more, more preferably 20 mm or more, even more preferably 40 mm or more, and further preferably 60 mm or more from the viewpoint of successful film formation. The distance between the nozzle and skin is preferably 160 mm or less, more preferably 150 mm or less, and even more preferably 120 mm or less. More specifically, the distance between the nozzle and skin is preferably 10 mm or more and 160 mm or less, more preferably 20 mm or more and 150 mm or less, even more preferably 40 mm or more and 150 mm or less, and further preferably 60 mm or more and 120 mm or less. The distance between the nozzle and skin can be determined, for example, by using a common non-contact sensor.

Whether or not the film formed by the electrostatic spraying method is porous, the film preferably has a basis weight of 0.05 $g/m^2$ or more, more preferably 0.1 $g/m^2$ or more, and even more preferably 1 $g/m^2$ or more, relative to 1 $m^2$ of skin. The basis weight is preferably 50 $g/m^2$ or less, more preferably 40 $g/m^2$ or less, even more preferably 30 $g/m^2$ or less, further preferably 25 $g/m^2$ or less, and furthermore preferably 20 $g/m^2$ or less. For example, the film preferably has a basis weight of 0.05 $g/m^2$ or more and 50 $g/m^2$ or less, more preferably 0.1 $g/m^2$ or more and 40 $g/m^2$ or less, even more preferably 0.1 $g/m^2$ or more and 30 $g/m^2$ or less, further preferably 0.1 $g/m^2$ or more and 25 $g/m^2$ or less, and furthermore preferably 1 $g/m^2$ or more and 20 $g/m^2$ or less, relative to 1 $m^2$ of skin. By setting the film basis weight within the above range, peeling off of the film due to an excess film thickness can be effectively suppressed.

Whether or not the film formed by the electrostatic spraying method is porous, the electrostatic spraying time in the electrostatic spraying method depends on the mixing ratios of components of a liquid composition and the voltage applied to the nozzle but is preferably 5 seconds or more and more preferably 10 seconds or more for 10 $cm^2$ of skin in view of effective suppression of peeling off of the film. The electrostatic spraying time in the electrostatic spraying method is preferably 120 seconds or less and more preferably 60 seconds or less. Specifically, the electrostatic spraying time in the electrostatic spraying method is preferably 5 seconds or more and 120 seconds or less and more preferably 10 seconds or more and 60 seconds or less.

The electrostatic spraying step of electrostatically spraying a liquid composition directly on skin means a step of performing electrostatic spraying directly on skin to form a film on the skin. The electrostatic spraying step differs from a series of the steps of electrostatically spraying a liquid composition on a site other than skin to form a sheet formed of fibers and applying or attaching the sheet onto skin.

In the present invention, either before or after the electrostatic spraying step of forming a film by the electrostatic spraying method or both before and after the electrostatic spraying step, the step of applying a cosmetic containing a powder onto the skin or the film may be further included. By performing the cosmetic-applying step before and/or after the electrostatic spraying step of forming a porous film formed of deposited fibers, color migration or adhesion of a cosmetic to clothes or the like can be suppressed even when the site of the skin or the film coated with the cosmetic containing a powder (hereinafter, the site is also called "cosmetic-applied site") is rubbed with clothes or the like. In contrast, the techniques described above in Background Art, i.e., the techniques disclosed in Patent Literatures 1 and 2 merely disclose the formation of a foundation film directly on the skin surface by the electrostatic spraying method but disclose no process of protecting the formed foundation film.

In the present invention, it is particularly preferred to apply a liquid composition onto a cosmetic-applied site to form a film, thereby covering the cosmetic surface to protect the cosmetic. In other words, the electrostatic spraying step of forming a film by the electrostatic spraying method described above is preferably performed after the cosmetic-applying step. In addition, the film is preferably formed over the whole region of a cosmetic-applied site in view of surely preventing color migration or adhesion of the cosmetic to a substance such as clothes coming into contact with skin and also in view of holding the cosmetic on the skin. In some cases, the film may be formed only in a part of the cosmetic-applied site. Alternatively, the film may be formed over both the cosmetic-applied site and the site without a cosmetic.

Examples of the cosmetic include preparations for external use exhibiting favorable effects on skin, such as a makeup cosmetic, a UV cosmetic, and a beauty essence. Examples of the makeup cosmetic include a base makeup cosmetic, a lip cosmetic, a makeup base, a BB cream, and a CC cream. Examples of the base makeup cosmetic include a foundation, a concealer, and a face powder. The base makeup cosmetic contains a color pigment, an extender pigment, or the like, and it is no essential difference which form the base makeup cosmetic is in, a liquid form, a gel form, an emulsion form, or a solid form.

In the cosmetic, the content of the powder varies according to purposes but is preferably 0.1% by mass or more and is preferably 100% by mass or less and more preferably 95% by mass or less in view of an improvement in adhesion between skin and the film formed by the electrostatic spraying method. In the present invention, the powder is preferably a color pigment or a pearl pigment in view of providing favorable effects on skin by the makeup cosmetic, the UV cosmetic, the beauty essence, or the like. In the present invention, the color pigment encompasses colored pigments and white pigments. From the same viewpoint, the color pigment preferably has an average particle diameter of 0.1 μm or more and more preferably more than 0.1 μm and is preferably 20 μm or less and more preferably 15 μm or less. The average particle diameter is a number average particle diameter determined with a laser diffraction/scattering particle size distribution analyzer LA-910 (manufactured by Horiba, Ltd.).

The color pigment and the extender pigment contained in the base makeup cosmetic may be any pigment used in common cosmetics. Examples include powders of inorganic substances such as silicic acid, silicic anhydride, magnesium silicate, talc, sericite, mica, kaolin, colcothar, clay, bentonite, isinglass, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, boron nitride, and composites thereof, powders of organic substances such as polyamide, nylon, polyester, polypropylene, polystyrene, polyurethane, a vinyl resin, a urea resin, a phenol resin, a fluorine resin, a silicon resin, an acrylic resin, a melamine resin, an epoxy resin, a polycarbonate resin, a divinylbenzene/styrene copolymer, silk powder, cellulose, a metal long-chain alkyl phosphate, an N-mono-long-chain alkyl acyl basic amino acid, and composites thereof; and composite powders of such an inorganic powder and such an organic powder. These extender pigments and color pigments have colors or no color (for example, white or essentially transparent) and can give the composition or skin at least one of the effects including coloring, light diffraction, oil absorption, translucency, opacity, gloss, an appearance without gloss, and smoothness.

The color pigment and the extender pigment contained in the cosmetic in the present invention may be any pigment used in common cosmetics. Examples include powders of inorganic substances such as silicic acid, silicic anhydride, magnesium silicate, talc, sericite, mica, kaolin, colcothar, clay, bentonite, isinglass, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, boron nitride, and composites thereof; powders of organic substances such as polyamide, nylon, polyester, polypropylene, polystyrene, polyurethane, a vinyl resin, a urea resin, a phenol resin, a fluorine resin, a silicon resin, an acrylic resin, a melamine resin, an epoxy resin, a polycarbonate resin, a divinylbenzene/styrene copolymer, silk powder, cellulose, a metal long-chain alkyl phosphate, an N-mono-long-chain alkyl acyl basic amino acid, and composites thereof; and composite powders of such an inorganic powder and such an organic powder. These extender pigments and color pigments have colors or no color (for example, white or essentially transparent) and can give the composition or skin at least one of the effects including coloring, light diffraction, oil absorption, translucency, opacity, gloss, an appearance without gloss, and smoothness.

In view of effectively preventing adhesion to clothes, the cosmetic preferably contains a color pigment or a pearl pigment. Examples of the color pigment include inorganic pigments such as titanium oxide, zinc oxide, yellow iron oxide, red iron oxide, black iron oxide, carbon black, ultramarine, iron blue, blue titanium oxide, black titanium oxide, chromium oxide, chromium hydroxide, and a titanium/titanium oxide sinter; organic pigments such as Red No. 201, Red No. 202, Red No. 226, Yellow No. 401, and Blue No. 404; lake pigments such as Red No. 104, Red No. 230, Yellow No. 4, Yellow No. 5, and Blue No. 1; and a pigment prepared by coating an organic pigment with a polymer such as a polymethacrylic acid ester. Examples of the pearl pigment include powders of inorganic substances such as mica titanium, colcothar-coated mica, bismuth oxychloride, titanium oxide-coated bismuth oxychloride, iron oxide-coated mica titanium, organic pigment-coated mica titanium, silicic acid/titanium-treated mica, titanium oxide-coated talc, silicon dioxide/colcothar-treated aluminum, and titanium oxide-coated glass powder; and flaky aluminum having a surface coated with an organic resin such as polyethylene terephthalate. These color pigments, extender pigments, and pearl pigments may be surface-treated with a fluorine compound or a silicone compound in view of endurance against sweat or sebum, for example.

In view of effectively preventing adhesion to clothes, the cosmetic preferably contains a color pigment or a pearl pigment. Examples of the color pigment include inorganic white pigments such as titanium oxide and zinc oxide; inorganic color pigments such as yellow iron oxide, red iron oxide, black iron oxide, carbon black, ultramarine, iron blue, blue titanium oxide, black titanium oxide, chromium oxide, chromium hydroxide, and a titanium/titanium oxide sinter; organic pigments such as Red No. 201, Red No. 202, Red No. 226, Yellow No. 401, and Blue No. 404; lake pigments such as Red No. 104, Red No. 230, Yellow No. 4, Yellow No. 5, and Blue No. 1; and a pigment prepared by coating an organic pigment with a polymer such as a polymethacrylic acid ester Examples of the pearl pigment include powders of inorganic substances such as mica titanium, colcothar-coated (titanium oxide/aluminum hydroxide) mixture, colcothar-coated mica, bismuth oxychloride, titanium oxide-coated bismuth oxychloride, iron oxide-coated mica titanium, organic pigment-coated mica titanium, silicic acid/ titanium-treated mica, titanium oxide-coated talc, silicon dioxide/colcothar-treated aluminum, and titanium oxide-coated glass powder; and flaky aluminum having a surface coated with an organic resin such as polyethylene terephthalate and a titanium oxide-yellow iron oxide-colcothar/lauryl methacrylate-dimethacrylic acid EG copolymer mixture.

Specifically, a cosmetic containing, as a color pigment, at least titanium oxide, yellow iron oxide, red iron oxide, or black iron oxide has an excellent makeup effect and can be effectively prevented from adhering to clothes. These color pigments and pearl pigments may be hydrophobically treated in view of endurance against sweat, sebum and the like. The hydrophobic treatment is preferably surface treatment such as fluorine compound treatment, silicone compound treatment, alkyl treatment, alkylsilane treatment, metallic soap treatment, water-soluble polymer treatment, amino acid treatment, N-acylamino acid treatment, lecithin treatment, organic titanate treatment, polyol treatment, acrylic resin treatment, methacrylic resin treatment, and urethane resin treatment. Specifically, a pigment surface-treated with a fluorine compound or a silicone compound is more preferred.

The color pigments and the pearl pigments may be used singly or in combination of two or more of them. In view of effectively preventing adhesion to clothes, the content in the total composition is preferably 0.1% by mass or more, more preferably 0.5% by mass or more, and even more preferably 1% by mass or more and is preferably 40% by mass or less, more preferably 30% by mass or less, and even more preferably 25% by mass or less. The content of the color pigment or the pearl pigment is preferably 0.1 to 40% by mass, more preferably 0.5 to 30% by mass, and even more preferably 1 to 25% by mass in the total composition.

The makeup cosmetic may further contain an oil that is liquid at 25° C., a wax that is solid at 25° C., or the like, in addition to the powder such as a color pigment and an extender pigment. The makeup cosmetic may further contain common components such as a thickener, a film forming agent, a surfactant, a sugar, a polyhydric alcohol, a water-soluble polymer, a sequestrant, a lower alcohol, an amino acid, an organic amine, a pH adjuster, a skin conditioner, a vitamin, an antioxidant, a fragrance chemical, and an antiseptic agent appropriately as long as the effects of the invention are not impaired.

The UV cosmetic preferably contains a component having ultraviolet protection ability, such as an ultraviolet absorber and an ultraviolet scattering agent. As the ultraviolet absorber, for example, one or more organic ultraviolet absorbers selected from benzophenone derivatives such as dihydroxybenzophenone, dihydroxydimethoxybenzophenone, hydroxymethoxybenzophenone sulfonate, and dihydroxydimethoxybenzophenone disulfonate and methoxycinnamic acid derivatives such as 2-ethylhexyl methoxycinnamate are preferred, and 2-ethylhexyl methoxycinnamate is more preferred. Examples of the ultraviolet scattering agent include zinc oxide microparticles, titanium oxide microparticles, and silica microparticles having an average particle diameter of 0.1 µm or less. Before or after the application of the cosmetic for the present invention onto skin, a cosmetic other than the cosmetic for the present invention may be applied onto skin.

In the present invention, before, after, or before and after the electrostatic spraying step of forming a film on skin by electrostatic spraying, a liquid agent application step of applying, onto skin or the film, a liquid agent that contains one or two or more substances selected from water, a polyol that is liquid at 20° C., and an oil that is liquid at 20° C. and differs from the above liquid composition may be performed in place of the above cosmetic application step. By performing the liquid agent application step, the film formed in the electrostatic spraying step is likely to fit with skin, and thus the film can be in closer contact with the skin and can also be transparent. For example, a level difference is unlikely to be formed between the film edge and skin, and this improves the adhesion between the film and the skin. As a result, the film is unlikely to be released or broken, for example. In addition, the color of a makeup cosmetic is unlikely to be hidden, a more natural appearance is achieved, and the presence of the film can be unlikely to be visualized. In a more preferred embodiment in which the film is a porous film including deposited fibers, the film has a high void ratio but has a high adhesion to skin and is likely to generate a large capillary force. When containing ultrafine fibers, the porous film can easily have a high specific surface area. The liquid agent application step can be performed by electrostatic spraying to apply a liquid agent onto skin or a film, but a liquid agent is preferably applied onto skin or a film by a method other than the electrostatic spraying, for example, by hand as described later from the viewpoint of simpleness.

In particular, by performing the electrostatic spraying step to form a porous film including deposited fibers and then performing the liquid agent application step, a liquid agent supporting film in which the liquid agent is among the fibers included in the porous film and/or on the fiber surface is formed. This improves the adhesion of the film and maintains or improves visual transparency of the film. When the film is particularly colorless and transparent or colored and transparent, the film is more unlikely to be visualized and thus can have a natural skin appearance. When the film is colored and transparent, the film looks transparent and thus can look like a part of the skin.

For the case where the liquid agent used in the liquid agent-applying step contains water, examples of the liquid agent include a liquid such as water, an aqueous solution, and an aqueous dispersion, a gel thickened by a thickener, a polar oil, an oil solution containing 10% by mass or more of a polar oil, and an emulsion containing a polar oil (O/W emulsions, W/O emulsions).

For the case where the liquid agent used in the liquid agent-applying step contains a polyol that is liquid at 20° C., examples of the polyol include alkylene glycols such as ethylene glycol, propylene glycol, 1,3-propanediol, and 1,3-butanediol; polyalkylene glycols such as diethylene glycol, dipropylene glycol, a polyethylene glycol having a weight average molecular weight of 2,000 or less, and a polypropylene glycol; and glycerols such as glycerol, diglycerol, and triglycerol. Of them, in view of sense of use including smoothness at the time of application, ethylene glycol, propylene glycol, 1,3-butanediol, dipropylene glycol, a polyethylene glycol having a weight average molecular weight of 2,000 or less, glycerol, and diglycerol are preferred; propylene glycol, 1,3-butanediol, and glycerol are more preferred; and propylene glycol and 1,3-butanediol are even more preferred.

For the case where the liquid agent used in the liquid agent-applying step contains an oil that is liquid at 20° C. (hereinafter, the oil is also called "liquid oil"), examples of the oil that is liquid at 20° C. include linear or branched hydrocarbon oils such as liquid paraffin, light isoparaffin, liquid isoparaffin, squalane, and squalene; ester oils such as a monohydric alcohol fatty acid ester, a polyhydric alcohol fatty acid ester, and a triglycerol fatty acid ester; and silicone oils such as dimethylpolysiloxane, dimethylcyclopolysiloxane, methylphenylpolysiloxane, methylhydrogenpolysiloxane, and a higher alcohol-modified organopolysiloxane. Of them, in view of sense of use including smoothness at the time of application, hydrocarbon oils and polar oils such as ester oils and silicone oils are preferred, and hydrocarbon oils and ester oils are more preferred. Liquid oils selected from these oils may be used singly or in combination of two or more of them.

Examples of the hydrocarbon oil include liquid paraffin, squalane, squalene, n-octane, n-heptane, cyclohexane, light isoparaffin, and liquid isoparaffin. In view of sense of use, liquid paraffin and squalane are preferred. In view of close contact of the electrostatically sprayed film with skin, the hydrocarbon oil preferably has a viscosity at 30° C. of 10 mPa·s or more and more preferably 30 mPa·s or more. From the same viewpoint, the total content of isododecane, isohexadecane, and hydrogenated polyisobutene, which have a viscosity at 30° C. of less than 10 mPa·s, in the liquid agent is preferably 10% by mass or less, more preferably 5% by mass or less, even more preferably 1% by mass or less, and further preferably 0.5% by mass or less, or such a component may not be contained.

Similarly, in view of close contact of the electrostatically sprayed film with skin, the ester oil and the silicone oil preferably have a viscosity at 30° C. of 10 mPa·s or more and more preferably 30 mPa·s or more.

The viscosity is determined at 30° C. by using a BM-type viscometer (manufactured by Tokimec, Inc., measurement conditions: with a rotor No. 1, at 60 rpm, for 1 minute).

From the same viewpoint, the total content of the ether oils such as cetyl 1,3-dimethylbutyl ether, dicaprylyl ether, dilauryl ether, and diisostearyl ether in the liquid agent is preferably 10% by mass or less, more preferably 5% by mass or less, and even more preferably 1% by mass or less.

As the liquid oil, a polar oil that is liquid at 20° C. can also be preferably used, and examples include ester oils, plant oils including ester oils (triglycerides), higher alcohols of branched fatty acids or unsaturated fatty acids, antiseptic agents, and silicone oil. These liquid oils may be used singly or in combination of two or more of them.

Examples of the ester oil include esters of a linear or branched fatty acid and a linear or branched alcohol or polyhydric alcohol and triglycerol fatty acid esters (triglycerides). Specific examples include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalenedicarboxylate, (C12 to 15)-alkyl benzoates, cetearyl isononanoate, glyceryl tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, tricoconut oil fatty acid glyceride, castor oil fatty acid methyl ester, oleyl oleate, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecy palmitate, 2-hexyldecyl adipate, diisopropyl sebacate, di-2-ethylhexyl succinate, triethyl citrate, 2-ethylhexyl p-methoxycinnamate, and tripropylene glycol dipivalate.

Of them, in view of close contact of the electrostatically sprayed film with skin and excellent feeling at the time of application onto skin, at least one selected from octyldodecyl myristate, myristyl myristate, isocetyl stearate, isocetyl isostearate, cetearyl isononanoate, diisobutyl adipate, di-2-ethylhexyl sebacate, isopropyl myristate, isopropyl palmitate, diisostearyl malate, neopentyl glycol dicaprate, (C12 to 15)-alkyl benzoates, and glyceryl tri(caprylate/caprate) is preferred; at least one selected from isopropyl myristate, isopropyl palmitate, diisostearyl malate, neopentyl glycol dicaprate, (C12 to 15)-alkyl benzoates, and glyceryl tri(caprylate/caprate) is more preferred; and at least one selected from neopentyl glycol dicaprate, (C12 to 15)-alkyl benzoates, and glyceryl tri(caprylate/caprate) is even more preferred.

The triglyceride is preferably a fatty acid triglyceride, which is contained, for example, in olive oil, jojoba oil, macadamia nut oil, meadowfoam oil, castor oil, safflower oil, sunflower oil, avocado oil, canola oil, apricot kernel oil, rice germ oil, or rice bran oil.

Examples of the higher alcohol include liquid higher alcohols having 12 to 20 carbon atoms, and specific examples include isostearyl alcohol and oleyl alcohol.

Examples of the antiseptic agent include phenoxyethanol, methyl p-hydroxybenzoate, ethyl p-aminobenzoate, isobutyl p-hydroxybenzoate, isopropyl p-hydroxybenzoate, ethyl p-hydroxybenzoate, butyl p-hydroxybenzoate, propyl p-hydroxybenzoate, benzyl p-hydroxybenzoate, and ethylhexanediol.

Examples of the silicone oil include dimethylpolysiloxane, dimethylcyclopolysiloxane, methylphenylpolysiloxane, methylhydrogenpolysiloxane, and a higher alcohol-modified organopolysiloxane.

The silicone oil preferably has a dynamic viscosity at 25° C. of 3 mm$^2$/s or more, more preferably 4 mm$^2$/s or more, and even more preferably 5 mm$^2$/s or more and is preferably 30 mm$^2$/s or less, more preferably 20 mm$^2$/s or less, and even more preferably 10 mm$^2$/s or less in view of close contact of the electrostatically sprayed film with skin.

Of them, dimethylpolysiloxane is preferably contained in view of close contact of the electrostatically sprayed film with skin.

The liquid agent preferably contains a liquid oil, and the content of the liquid oil in the liquid agent is preferably 0.1% by mass or more, more preferably 0.5% by mass or more, and even more preferably 5% by mass or more. The content is preferably 100% by mass or less. The content of the liquid oil in the liquid agent is preferably 0.1% by mass or more and 100% by mass or less and more preferably 0.5% by mass or more and 100% by mass or less.

Particularly, when the liquid agent contains a polar oil, the liquid agent preferably contains water with the polar oil in view of an improvement in adhesion of a film to skin, and the total content of water and the polar oil in the liquid agent is preferably 40% by mass or more and 100% by mass or less. The liquid agent may contain a surfactant, a polymer, or a thickener in view of stability, and may contain an oily substance that is solid at 30° C., such as vaseline, cetanol, stearyl alcohol, and ceramide, in view of an improvement in adhesion to skin or in moisturization performance of a film.

Similarly, when the liquid agent contains a polyol, the liquid agent preferably contains water with the polyol in view of an improvement in adhesion of a film to skin, and the total content of water and the polyol in the liquid agent is preferably 40% by mass or more and 100% by mass or less. The liquid agent may contain a surfactant, a polymer, or a thickener in view of stability, and may contain an oily substance that is solid at 30° C., such as vaseline, cetanol, stearyl alcohol, and ceramide, in view of an improvement in adhesion to skin or in moisturization performance of a film.

Even when the liquid agent contains any of water, a polyol that is liquid at 20° C., and a liquid oil, the liquid agent preferably has a viscosity of about 5,000 mPa·s or less at 25° C. in view of an improvement in adhesion between the film formed by the electrostatic spraying method and a cosmetic-applied site. The measurement method of the viscosity of a liquid is as described above.

The content of the color pigment in the liquid agent is preferably less than 0.1% by mass, more preferably 0.05% by mass or less, even more preferably 0.01% by mass or less, and further preferably 0.001% by mass or less in view of an improvement in adhesion between skin and the film formed by the electrostatic spraying method. In the present invention, the color pigment excludes transparent pigments, and a white pigment is included in the color pigment.

To apply a liquid agent containing water, a polyol, or a liquid oil onto skin, various methods can be used. For example, the liquid agent is applied onto skin by dropping, sprinkling, or another method, and then spread. Such steps enable the liquid agent to fit with the skin or a film, forming a thin layer of the liquid agent. The liquid agent-spreading step can be performed by rubbing with the finger(s) of a user or a tool such as an applicator. Although the liquid agent may be simply dropped or sprinkled, the spreading step enables fitting the liquid agent with skin or a film, and the film adhesion can be sufficiently improved. As an alternative method, the liquid agent may be sprayed on skin to form a thin layer of the liquid agent. In this case, spreading is not required additionally, but spreading after spraying is acceptable. When the liquid agent is applied after film formation, a sufficient amount of the liquid agent can be applied onto skin, and a sheet material can be brought into contact with the area with the liquid agent to remove an excess liquid agent.

The amount of the liquid agent applied onto skin is an amount necessary and sufficient for an improvement in adhesion between the skin and a film. When the liquid agent contains a liquid oil, the amount of the liquid agent applied onto skin is such an amount that the basis weight of the liquid oil relative to 1 m$^2$ of skin is preferably 0.1 g/m$^2$ or more and more preferably 0.2 g/m$^2$ or more and is preferably 40 g/m$^2$ or less and more preferably 35 g/m$^2$ or less from the viewpoint of sufficient adhesion between skin and a film. For example, the amount of the liquid agent applied to skin is such an amount that the basis weight of the liquid oil relative to 1 m$^2$ of skin is preferably 0.1 g/m$^2$ or more and 40 g/m$^2$ or less and more preferably 0.2 g/m$^2$ or more and 35 g/m$^2$ or less.

The amount of the liquid agent applied to skin or a film is preferably 5 g/m$^2$ or more, more preferably 10 g/m$^2$ or more, and even more preferably 15 g/m$^2$ or more and is preferably 50 g/m$^2$ or less and more preferably 45 g/m$^2$ or less from the viewpoint of an improvement in adhesion between skin and a film and an improvement in transparency.

Before or after the application of the liquid agent onto skin, a cosmetic other than the liquid agent may be applied onto skin.

In the present invention, before, after, or before and after the electrostatic spraying step of forming a film on skin by electrostatic spraying, both the cosmetic-applying step and the liquid agent-applying step may be performed. In this case, the steps may be performed in any order, but it is preferred that after the cosmetic-applying step, the electrostatic spraying step be performed, and that after the electrostatic spraying step, the liquid agent-applying step be performed. By forming a film in this step order, color migration or adhesion of a cosmetic to clothes or the like by rubbing or the like of a cosmetic-applied site can be effectively prevented, and a film formed in the electrostatic spraying step is likely to fit with the cosmetic-applied site. The film can be thus in closer contact with the skin and can also be transparent. A level difference is unlikely to be formed between the film edge and skin, and this improves the adhesion between the film and the skin. As a result, the film is unlikely to peel off or be broken, for example. In addition, the color of a makeup cosmetic is unlikely to be hidden, thereby providing a more natural appearance, and the presence of the film can be unlikely to be visualized.

The method for producing a film as described above is useful as various beauty methods excluding a surgery method, a therapeutic treatment method, or a diagnostic method for human bodies. For example, the method for producing a film of the present invention can be applied to beauty care for skin whitening in an application site, concealment of skin blotches, concealment of skin darkening/shadow, concealment of skin wrinkles, skin shading, protection of skin from ultraviolet light, and skin moisturization. In addition, the method for producing a film of the present invention can also be applied to various processes for skin protection performed personally in home, including protection of various wounds such as abraded wound, cut wound, laceration, and stab wound and prevention of bedsore.

The present invention has been described on the basis of the preferred embodiments thereof, but the present invention is not limited to the above embodiments. For example, in the above embodiment, a person intended to form a film on the skin thereof holds the electrostatic spray device 10 to form an electric field between the conductive nozzle of the apparatus 10 and the skin of the person, but a person intended to form a film on the skin thereof does not need to hold the electrostatic spray device 10 as long as an electric field is formed therebetween.

In consideration of the above embodiments, the present invention further discloses the following methods for producing a film.

<1>

A method for producing a film includes an electrostatic spraying step of electrostatically spraying a liquid composition directly on a surface of skin to form a film on the skin by using an electrostatic spray device. The electrostatic spray device includes a container capable of storing the liquid composition, a nozzle configured to eject the liquid composition, and a power supply configured to apply a voltage to the nozzle.

The liquid composition contains component (a), component (b), and component (c):

(a) one or two or more volatile substances selected from alcohols and ketones, (b) a water-insoluble polymer having film formability, and (c) 0.2% by mass or more and 25% by mass or less of water.

In the electrostatic spraying step, the power supply applies a voltage of 5 kV or more and 50 kV or less to the nozzle that ejects the liquid composition at a flow rate of 0.4 mL/h or more and 30 mL/h or less to perform electrostatic spraying on the surface of the skin, and a ratio of the flow rate F (mL/h) to the voltage P (kV) (flow rate F/voltage P) is 0.8 or less.

<2>
The method for producing a film as set forth in clause <1>, in which the liquid composition has a viscosity at 25° C. of 5 mPa·s or more and 3,000 mPa·s or less.

<3>
The method for producing a film as set forth in clause <1> or <2>, in which the component (b) is at least one selected from the group consisting of a partially saponified polyvinyl alcohol, a low-saponified polyvinyl alcohol, a completely saponified polyvinyl alcohol, a polyvinyl butyral resin, a polymethacrylic acid resin, polyvinylacetal diethylaminoacetate, an oxazoline-modified silicone, and polylactic acid.

<4>
The method for producing a film as set forth in any one of clauses <1> to <3>, in which the liquid composition contains the component (b) at a content of 2% by mass or more and 20% by mass or less.

<5>
The method for producing a film as set forth in any one of clauses <1> to <4>, in which the component (b) and the component (c) are contained at a content mass ratio (b/c) of 0.4 or more and 50 or less.

<6>
The method for producing a film as set forth in any one of clauses <1> to <5>, in which in the electrostatic spraying step, a distance between the nozzle and the skin is 10 mm or more and 160 mm or less.

<7>
The method for producing a film as set forth in any one of clauses <1> to <6>, in which the liquid composition has a conductivity at 25° C. of 8 μS/cm or more and 260 μS/cm or less.

<8>
The method for producing a film as set forth in any one of clauses <1> to <7>, in which in the electrostatic spraying step, the film has a basis weight of 0.05 g/m² or more and 50 g/m² or less relative to 1 m² of the skin.

<9>
The method for producing a film as set forth in any one of clauses <1> to <8>, in which in the electrostatic spraying step, the liquid composition is electrostatically sprayed on skin to form a porous film including deposited fibers.

<10>
The method for producing a film as set forth in any one of clauses <1> to <9> includes the electrostatic spraying step and a liquid agent application step of applying, onto skin, a liquid agent containing one or two or more substances selected from water, a polyol, and an oil that is liquid at 20° C., and the liquid agent differs from the liquid composition.

<11>
The method for producing a film as set forth in clause <10>, in which in the electrostatic spraying step, a porous film including deposited fibers is formed, and then in the liquid agent application step, the liquid agent is applied onto the porous film to form a liquid agent supporting film in which the liquid agent is among the fibers included in the porous film and/or on a fiber surface.

<12>
The method for producing a film as set forth in clause <10> or <11>, in which in the liquid agent application step, the liquid agent is applied onto the film, and the film maintains transparency.

<13>
The method for producing a film as set forth in any one of clauses <1> to <12> further includes a cosmetic application step of applying a cosmetic containing a powder onto a surface of skin, and after the cosmetic application step, the electrostatic spraying step is included.

<14>
The method for producing a film as set forth in any one of clauses <1> to <13>, in which the electrostatic spray device further includes a housing, and the housing stores the container, the nozzle, and the power supply and is to be held by one hand.

<15>
The method for producing a film as set forth in any one of clauses <1> to <14>, in which the electrostatic spray device includes a cartridge and a main body,
the cartridge includes the container, a gasket slidable along an inner surface of the container, and the nozzle configured to eject the liquid composition from the container,
the main body includes a power source configured to eject the liquid composition and a power transmitter configured to transmit a motive power from the power source to the cartridge,
the power transmitter electrically insulates the power source from the cartridge, and
the cartridge is detachable from the main body.

<16>
The method for producing a film as set forth in any one of clauses <1> to <14>, in which the electrostatic spray device includes a cartridge and a main body,
the cartridge includes a container capable of storing the liquid composition and deformable according to an internal pressure, the nozzle, and a pump configured to feed the liquid composition stored in the container to the nozzle,
the main body includes a power source configured to drive the pump to eject the liquid composition and a power transmitter configured to transmit a motive power from the power source to the pump,
the power transmitter electrically insulates the power source from the cartridge, and
the cartridge is detachable from the main body.

<17>
The method for producing a film as set forth in clause <16>, in which the container is detachable from the cartridge.

<18>
The method for producing a film as set forth in any one of clauses <15> to <17>, in which the container has a volume of 1 mL or more and 20 mL or less.

<19>
The method for producing a film as set forth in any one of clauses <1> to <18>, in which the nozzle has a microspace that has a cross-sectional size of 100 μm or more and 1,400 μm or less.

<20>
The method for producing a film as set forth in any one of clauses <1> to <19>, in which the nozzle has a flow path length of 1 mm or more and 25 mm or less.

<21>
The method for producing a film as set forth in any one of clauses <1> to <20>, in which in the electrostatic spraying step, the power supply applies a voltage of 9 kV or more and 30 kV or less to the nozzle that ejects the liquid composition at a flow rate of 0.4 mL/h or more and 12 mL/h or less to perform electrostatic spraying on a surface of skin, such that a ratio of the flow rate F (mL/h) to the voltage P (kV) (flow rate F/voltage P) is 0.06 or more and 0.6 or less.

<22>

The method for producing a film as set forth in any one of clauses <1> to <20>, in which in the electrostatic spraying step, the power supply applies a voltage of 9 kV or more and 30 kV or less to the nozzle that ejects the liquid composition to perform electrostatic spraying on a surface of skin, such that a relation between the voltage P (kV) and the flow rate F (mL/h) is (1≤F≤0.3P+2.5).

<23>

A method for producing a film includes an electrostatic spraying step of electrostatically spraying a liquid composition directly on a surface of skin to form a film on the skin by using an electrostatic spray device.

The electrostatic spray device includes a cartridge and a main body, the cartridge includes a container capable of storing the liquid composition, a gasket slidable along an inner surface of the container, and a nozzle configured to eject the liquid composition from the container, the main body includes a power source configured to eject the liquid composition and a power transmitter configured to transmit a motive power from the power source to the cartridge, the power transmitter electrically insulates the power source from the cartridge, and the liquid composition contains component (a) and component (b):

(a) one or two or more volatile substances selected from alcohols and ketones; and (b) a polymer having film formability.

<24>

The method for producing a film as set forth in clause <23>, in which the liquid composition further contains water as component (c), and the component (b) and the component (c) are contained at a content mass ratio (b/c) of 0.4 or more and 140 or less.

<25>

The method for producing a film as set forth in clause <23> or <24>, in which the cartridge is detachable from the main body.

<26>

The method for producing a film as set forth in any one of clauses <23> to <25>, in which in the electrostatic spraying step, the liquid composition is electrostatically sprayed on skin to form a porous film including deposited fibers.

<27>

The method for producing a film as set forth in any one of clauses <23> to <26> includes the electrostatic spraying step and a liquid agent application step of applying, onto skin, a liquid agent containing one or two or more substances selected from water, a polyol, and an oil that is liquid at 20° C., and the liquid agent differs from the liquid composition.

<28>

The method for producing a film as set forth in clause <27>, in which in the electrostatic spraying step, a porous film including deposited fibers is formed, and then in the liquid agent application step, the liquid agent is applied onto the porous film to form a liquid agent supporting film in which the liquid agent is among the fibers included in the porous film and/or on a fiber surface.

<29>

The method for producing a film as set forth in clause <27> or <28>, in which in the liquid agent application step, the liquid agent is applied onto the film, and the film maintains transparency.

<30>

The method for producing a film as set forth in any one of clauses <23> to <29> further includes a cosmetic application step of applying a cosmetic containing a powder onto a surface of skin, and after the cosmetic application step, the electrostatic spraying step is included.

<31>

The method for producing a film as set forth in any one of clauses <23> to <30>, in which the electrostatic spray device further includes a housing, and the housing stores the cartridge and the main body and is to be held by one hand.

<32>

A method for producing a film includes an electrostatic spraying step of electrostatically spraying a liquid composition directly on a surface of skin to form a film on the skin by using an electrostatic spray device.

The electrostatic spray device includes a cartridge and a main body, the cartridge includes a container capable of storing the liquid composition and deformable according to an internal pressure, a nozzle configured to eject the liquid composition, and a pump configured to feed the liquid composition stored in the container to the nozzle, the main body includes a power source configured to drive the pump to eject the liquid composition and a power transmitter configured to transmit a motive power from the power source to the pump, the power transmitter electrically insulates the power source from the cartridge, and the liquid composition contains component (a) and component (b):

(a) one or two or more volatile substances selected from alcohols and ketones; and (b) a polymer having film formability.

<33>

The method for producing a film as set forth in clause <32>, in which the liquid composition further contains water as component (c), and the component (b) and the component (c) are contained at a content mass ratio (b/c) of 0.4 or more and 50 or less.

<34>

The method for producing a film as set forth in clause <32> or <33>, in which the cartridge is detachable from the main body.

<35>

The method for producing a film as set forth in any one of clauses <32> to <34>, in which the container is detachable from the cartridge.

<36>

The method for producing a film as set forth in any one of clauses <32> to <35>, in which in the electrostatic spraying step, the liquid composition is electrostatically sprayed on skin to form a porous film including deposited fibers.

<37>

The method for producing a film as set forth in any one of clauses <32> to <36> includes the electrostatic spraying step and a liquid agent application step of applying, onto skin, a liquid agent containing one or two or more substances selected from water, a polyol, and an oil that is liquid at 20° C.

<38>

The method for producing a film as set forth in clause <37>, in which in the electrostatic spraying step, a porous film including deposited fibers is formed, and then in the liquid agent application step, the liquid agent is applied onto the porous film to form a liquid agent supporting film in which the liquid agent is among the fibers included in the porous film and/or on a fiber surface.

<39>

The method for producing a film as set forth in clause <37> or <38>, in which in the liquid agent application step, the liquid agent is applied onto the film, and the film maintains transparency.

<40>

The method for producing a film as set forth in any one of clauses <32> to <39> further includes a cosmetic application step of applying a cosmetic containing a powder onto a surface of skin, and after the cosmetic application step, the electrostatic spraying step is included.

<41>

The method for producing a film as set forth in any one of clauses <32> to <40>, in which the electrostatic spray device further includes a housing, and the housing stores the cartridge and the main body and is to be held by one hand.

EXAMPLES

The present invention will next be described in further detail with reference to examples. However, the scope of the invention is not limited to the examples. Unless otherwise specified, "%" and "part" mean "% by mass" and "part by mass", respectively.

Example 1-1

(1) Preparation of Liquid Composition

As the component (a) of a liquid composition, 99.5% ethanol (manufactured by Wako Pure Chemical Industries, Ltd.) was used, as the component (b), polyvinyl butyral (manufactured by SEKISUI CHEMICAL CO., LTD., S-LEC B BM-1) was used, and as the component (c), ion-exchanged water was used. The mixing ratio of the components is as shown in Table 1. These components were stirred at ordinary temperature for about 12 hours by using a propeller mixer to give a homogeneous transparent mixed solution. The solution was used as a liquid composition.

(2) Electrostatic Spraying Step

An electrostatic spray device 10 having the configuration shown in FIG. 1 and having the appearance shown in FIG. 7 was used to perform electrostatic spraying method for 20 seconds toward a skin model (artificial leather, PROTEIN LEATHER PBZ13001BK, manufactured by Idemitsu Technofine Co., Ltd.) cutout into a size of 50 mm×50 mm. The electrostatic spraying method was performed in the following conditions.

Applied voltage: 30 kV
Distance between the nozzle and the skin model: 100 mm
Liquid composition ejection speed (flow rate): 4 mL/h
Nozzle diameter: 0.3 mm
Environment: 25° C., 40% RH Examples 1-2 and 1-3

The electrostatic spraying step was performed in a similar manner to that in Example 1-1 except that conditions shown in Table 1 were adopted, giving porous films including deposited fibers.

Example 1-4

The components (a) to (c) and distearyldimonium chloride as component (d) were mixed in conditions shown in Table 1. The electrostatic spraying step was performed in a similar manner to that in Example 1-1 except that the applied voltage was 10 kV, and the ejection flow rate was 5 mL/h, giving a porous film including deposited fibers.

Example 1-5

Polyvinyl butyral and an acrylic acid polymer were used as the component (b), and the components (a) to (c) were mixed in conditions shown in Table 1. The electrostatic spraying step was performed in a similar manner to that in Example 1-1 except that the ejection flow rate was 3 mL/h, giving a porous film including deposited fibers.

Comparative Example 1-1

The electrostatic spraying step was performed in a similar manner to that in Example 1-1 except that conditions shown in Table 1 were adopted, and the ejection flow rate was 0.05 mL/h, giving a porous film including deposited fibers.

Comparative Example 1-2

The electrostatic spraying step was performed in a similar manner to that in Example 1-1 except that conditions shown in Table 1 were adopted, and the applied voltage was 3 kV, giving a porous film including deposited fibers.

[Evaluation of Film Formability]

In the electrostatic spray device 10 shown in FIG. 1, the liquid composition prepared at a ratio in Table 1 was packed, and electrostatic spraying was performed on a skin model for 20 seconds. The film formability was visually evaluated on the basis of the following criteria. Table 1 shows the results.

○: A film is stably formed for 1 minute or more.
x: Spinning is unstable, and no film is formed, or a film has unevenness.

TABLE 1

| | Component (% by mass) | Example 1-1 | Example 1-2 | Example 1-3 | Example 1-4 | Example 1-5 | Comparative Example 1-1 | Comparative Example 1-2 |
|---|---|---|---|---|---|---|---|---|
| (a) | Ethanol | 89.5 | 85 | 72 | 84.08 | 82.72 | 89.5 | 89.5 |
| (b) | Polyvinyl butyral (*1) | 10 | 10 | 10 | 15 | 12 | 10 | 10 |
| | Acrylic acid polymer (*2) | | | | | 3.6 | | |

TABLE 1-continued

|   | Component (% by mass) | Example 1-1 | Example 1-2 | Example 1-3 | Example 1-4 | Example 1-5 | Comparative Example 1-1 | Comparative Example 1-2 |
|---|---|---|---|---|---|---|---|---|
| (c) | Water | 0.5 | 5 | 18 | 0.42 | 1.68 | 0.5 | 0.5 |
| (d) | Distearyldimonium chloride (*3) | | | | 0.5 | | | |
|   | Total amount | 100.0 | 100.0 | 100.0 | 100.0 | 100.0 | 100.0 | 100.0 |
| Content mass ratio | Component (b)/component (c) | 20 | 2 | 0.6 | 35.7 | 7.1 | 20.0 | 20.0 |
|   | Component (b)/component (a) | 0.11 | 0.12 | 0.14 | 0.18 | 0.15 | 0.11 | 0.11 |
|   | Component (a)/component (c) | 179 | 17 | 4 | 200 | 49 | 179 | 179 |
|   | Viscosity (mPa · s) | 51.9 | 55.7 | 61.4 | 256 | Not measured | 51.9 | 51.9 |
|   | Applied voltage (kV) | 30 | 30 | 30 | 10 | 30 | 30 | 3 |
|   | Ejection flow rate (mL/h) | 4 | 4 | 4 | 5 | 3 | 0.05 | 4 |
|   | Formability evaluation | ○ | ○ | ○ | ○ | ○ | x | x |

(*1) S-LEC B BM-1 (SEKISUI CHEMICAL CO., LTD.)
(*2) MAS683, water-insoluble acrylic polymer, CosMED Pharmaceutical Co., Ltd.
(*3) VARISOFT TA100 (Evonik Japan)

As apparent from the results shown in Table 1, the electrostatic spray device used in the present invention can stably form films. The film formed in each example is revealed to have high adhesion to the skin model.

Examples 1-6 to 1-9 and Comparative Example 1-3

The components (a), (b), and (c) were mixed at the same ratio as in Example 1-2, giving a liquid composition. The obtained liquid composition and an electrostatic spray device 10 having the configuration shown in FIG. 2 and having the appearance shown in FIG. 7 were used to perform electrostatic spraying method for 30 seconds toward a skin model (artificial leather, PROTEIN LEATHER PBZ13001BK, manufactured by Idemitsu Technofine Co., Ltd.) cutout into a size of 50 mm×50 mm. The electrostatic spraying method was performed in conditions as shown in Table 2 except that the nozzle diameter was 0.3 mm, and the electrostatic spraying environment was 23.5° C. and 30% RH.

Examples 1-10 and 1-11

The electrostatic spraying step was performed in a similar manner to that in Example 1-6 except that a polyurethane resin (manufactured by Covestro Deutschland AG, Baycusan C2000) was used as the component (b), and conditions and spray conditions shown in Table 2 were adopted, giving porous films including deposited fibers. The electrostatic spraying method was performed in the following conditions.

Applied voltage: 30 kV
Distance between the nozzle and the skin model: 100 mm
Liquid composition ejection speed (flow rate): 5 mL/h
Nozzle diameter: 0.3 mm
Environment: 25° C., 70% RH

[Evaluation of Film Formability]

In the electrostatic spray device 10 shown in FIG. 2, the liquid composition prepared at a ratio in Table 2 was packed, and electrostatic spraying was performed on a skin model for 30 seconds. The film formability was visually evaluated on the basis of the following criteria. Table 2 shows the results.

○: A film is satisfactory formed on a skin model.

xx: Liquid drops of the liquid composition were ejected, and a film has unevenness.

TABLE 2

|   | Component (% by mass) | Example 1-6 | Example 1-7 | Example 1-8 | Example 1-9 | Example 1-10 | Example 1-11 | Comparative Example 1-3 |
|---|---|---|---|---|---|---|---|---|
| (a) | Ethanol | 85 | 85 | 85 | 85 | 74.13 | 59.40 | 85 |
| (b) | Polyvinyl butyral (*1) | 10 | 10 | 10 | 10 | | | 10 |
|   | Polyurethane resin (*6) | | | | | 25.00 | 39.80 | |
| (c) | Water | 5 | 5 | 5 | 5 | 0.37 | 0.30 | 5 |
| (d) | Distearyldimonium chloride (*3) | | | | | 0.50 | 0.50 | |
|   | Total amount | 100 | 100 | 100 | 100 | 100 | 100 | 100 |
| Content mass ratio | Component (b)/component (c) | 2 | 2 | 2 | 2 | 67.6 | 132.7 | 2 |
|   | Component (b)/component (a) | 0.12 | 0.12 | 0.12 | 0.12 | 0.34 | 0.67 | 0.12 |
|   | Component (a)/component (c) | 17 | 17 | 17 | 17 | 200.4 | 198.0 | 17 |
|   | Applied voltage (kV) | 30 | 30 | 20 | 20 | 30 | 30 | 10 |
|   | Ejection flow rate (mL/h) | 10 | 10 | 8 | 7 | 5 | 5 | 10 |
|   | Distance from nozzle to skin (mm) | 100 | 70 | 70 | 100 | 100 | 100 | 70 |
|   | Flow rate (mL/h)/voltage (kV) | 0.33 | 0.33 | 0.40 | 0.35 | 0.17 | 0.17 | 1.0 |
|   | Formability evaluation | ○ | ○ | ○ | ○ | ○ | ○ | xx |

(*1) S-LEC B BM-1 (SEKISUI CHEMICAL CO., LTD.)
(*3) VARISOFT TA100 (Evonik Japan)
(*6) Baycusan C2000 40% (Covestro Deutschland AG)

As apparent from the results shown in Table 2, the film in each example can be stably formed by the electrostatic spray device shown in FIG. 1. The films in Examples 1-6 to 1-9 are revealed to have higher adhesion to the skin model than the film in Comparative Example 1-3.

Example 2-1

(1) Preparation of Liquid Composition

As the component (a) of a liquid composition, 99.5% ethanol (manufactured by Wako Pure Chemical Industries, Ltd.) was used, as the component (b), polyvinyl butyral (manufactured by SEKISUI CHEMICAL CO., LTD., S-LEC B BM-1) was used, and as the component (c), ion-exchanged water was used. As for the mixing ratio of each component, the component (a) was 79.5%, the component (b) was 14%, and the component (c) was 0.5%. These components were stirred at ordinary temperature for about 12 hours by using a propeller mixer to give a homogeneous transparent mixed solution. The solution was used as a liquid composition.

(2) Electrostatic Spraying Step

An electrostatic spray device 10 having the configuration shown in FIG. 2 and FIG. 3 and having the appearance shown in FIG. 7 was used to perform electrostatic spraying method for 20 seconds toward a skin model (artificial leather, PROTEIN LEATHER PBZ13001BK, manufactured by Idemitsu Technofine Co., Ltd.) cutout into a size of 50 mm×50 mm. As the screw shaft 171 and the feed screw 172 in the main body 10B of the electrostatic spray device 10 shown in FIG. 2 and FIG. 3, nonconductive plastic members were used. The electrostatic spraying method was performed in the following conditions.

Applied voltage: 10 kV
Distance between the nozzle and the skin model: 100 mm
Liquid composition ejection speed: 5 mL/h
Nozzle diameter: 0.3 mm
Environment: 25° C., 40% RH Examples 2-2 to 2-6

The electrostatic spraying step was performed in a similar manner to that in Example 2-1 except that conditions shown in Table 3 were adopted, giving porous films including deposited fibers.

[Insulating Property Evaluation]

A liquid composition of Example or Comparative Example was packed to the tip of the nozzle 15, then a voltage of 10 kV was applied to the nozzle 15, and the leakage current was measured. Table 3 shows the results. The criteria are as shown below.

○: The leakage current was not more than 0.1 mA.
x: The leakage current was more than 0.1 mA.

[Spinning Performance Evaluation]

In an electrostatic spray device 10 shown in FIG. 2, the liquid composition prepared at a ratio in Table 3 was packed, and electrostatic spraying was performed. The spinning performance was visually evaluated on the basis of the following criteria. Table 3 shows the results.

○: A film is stably formed for 1 minute or more.
x: Spinning is unstable, and no film is formed.

[Adhesion Evaluation]

The adhesion of each film formed in Examples and Comparative Examples to a skin model was evaluated. For the adhesion evaluation, a micro-vibration load was applied to a film by a finger touching a skin model in a perpendicular direction, and a shear force was applied to the film by a finger reciprocating in a parallel direction with the skin model. The film state was then visually observed to evaluate the adhesion. Table 3 shows the results. The criteria are as shown below.

1: When a micro-vibration load is applied by a finger in a perpendicular direction, the film is almost completely released.

2: When a micro-vibration load is applied by a finger in a perpendicular direction, some fibers included in the film are released.

3: A film is not released by a load in the perpendicular direction, but is almost completely released when a shear force is applied in a parallel direction.

4: A film is not released by a load in the perpendicular direction, but a part of the film or some of the fibers are released when a shear force is applied by a finger in a parallel direction.

5: A film is not released by a load in the perpendicular direction, and the film or fibers are not released even when a shear force is applied in a parallel direction.

TABLE 3

| | Component (% by mass) | Example 2-1 | Example 2-2 | Example 2-3 | Example 2-4 | Example 2-5 | Example 2-6 |
|---|---|---|---|---|---|---|---|
| (a) | Ethanol | 79.5 | 79.5 | 79.2 | 66.3 | 66.7 | 42.5 |
| | 1-Butanol | | | | | | 31.5 |
| | 2-Propanol | | | | | | |
| (b) | Polyvinyl butyral | 14 | | 14 | 10 | 10 | |
| | Polyvinylacetal diethylaminoacetate | | 14 | | | | |
| | Alkyl acrylate/octylacrylamide copolymer | | | | | | 20.5 |
| (c) | Water | 0.5 | 0.5 | 0.8 | 0.7 | 0.3 | 0.5 |
| Other component | Di(phytosteryl/octyldodecyl) lauroyl glutamate | 6 | 6 | 6 | | | |
| | Glycerol | | | | 23 | | |
| | Polyglyceryl-2 diisostearate | | | | | 23 | 5 |
| | Total amount | 100.0 | 100.0 | 100.0 | 100.0 | 100.0 | 100.0 |
| Content mass ratio | Component (a)/component (c) | 159.0 | 159.0 | 99.0 | 94.7 | 222.3 | 148.0 |
| | Component (b)/component (c) | 28.0 | 28.0 | 17.5 | 14.3 | 33.3 | 41.0 |
| | Insulating property evaluation | ○ | ○ | ○ | ○ | ○ | ○ |
| | Spinning performance evaluation | ○ | ○ | ○ | ○ | ○ | ○ |
| | Adhesion evaluation | 4 | 4 | 4 | 4 | 4 | 3 |

As apparent from the results shown in Table 3, the electrostatic spray device of the present invention having the structure shown in FIG. 2 and FIG. 3 has high insulating properties and can perform stable spinning. The films formed in Examples are revealed to have high adhesion to the skin model.

[Example 3-1]

(1) Preparation of liquid composition

As the component (a) of a liquid composition, 99.5% ethanol (manufactured by Wako Pure Chemical Industries, Ltd.) was used, as the component (b), polyvinyl butyral (manufactured by SEKISUI CHEMICAL CO., LTD., S-LEC B BM-1) was used, and as the component (c), ion-exchanged water was used. As for the mixing ratio of each component, the component (a) was 79.5%, the component (b) was 14%, and the component (c) was 0.5%. These components were stirred at ordinary temperature for about 12 hours by using a propeller mixer to give a homogeneous transparent mixed solution. The solution was used as a liquid composition.

(2) Electrostatic spraying step

Figure 5:
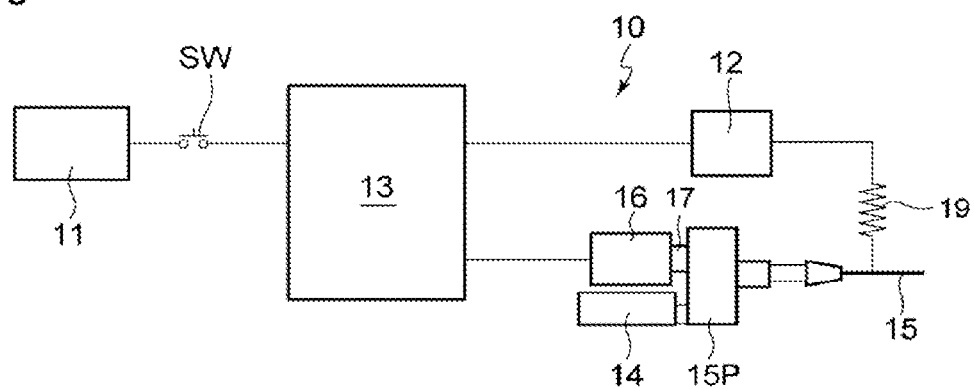
FIG. 5 is a schematic view showing the configuration of another embodiment of the electrostatic spray device used in the present invention.

An electrostatic spray device 10 having the configuration shown in FIG. 5 and FIG. 6 and having the appearance shown in FIG. 7 was used to perform electrostatic spraying method for 20 seconds toward a skin model (artificial leather, PROTEIN LEATHER PBZ13001BK, manufactured by Idemitsu Technofine Co., Ltd.) cutout into a size of 50 mm×50 mm. As the power transmitter 17, a nonconductive plastic member was used. The electrostatic spraying method was performed in the following conditions.
Applied voltage: 10 kV
Distance between the nozzle and the skin model: 100 mm
Liquid composition ejection speed: 5 mL/h
Nozzle diameter: 0.3 mm
Environment: 25° C., 40% RH

[Examples 3-2 to 3-6]

The electrostatic spraying step was performed in a similar manner to that in Example 3-1 except that conditions shown in Table 4 were adopted, giving porous films including deposited fibers.

[Insulating Property Evaluation]

A liquid composition of Example or Comparative Example was packed to the tip of the nozzle 15, then a voltage of 10 kV was applied to the nozzle 15, and the leakage current was measured. Table 4 shows the results. The criteria are as shown below.
○: The leakage current was not more than 0.1 mA.
x: The leakage current was more than 0.1 mA.

[Spinning performance evaluation]

In an electrostatic spray device 10 shown in FIG. 5 and FIG. 6, the liquid composition prepared at a rate in Table 4 was packed, and electrostatic spraying was performed. The spinning performance was visually evaluated on the basis of the following criteria. Table 4 shows the results.
○: A film is stably formed for 1 minute or more.
x: Spinning is unstable, and no film is formed.

[Adhesion Evaluation]

The adhesion of each film formed in Examples and Comparative Examples to a skin model was evaluated. For the adhesion evaluation, a micro-vibration load was applied to a film by a finger touching a skin model in a perpendicular direction, and a shear force was applied to the film by a finger reciprocating in a parallel direction with the skin model. The film state was then visually observed to evaluate the adhesion. Table 4 shows the results. The criteria are as shown below.

1: When a micro-vibration load is applied by a finger in a perpendicular direction, the film is almost completely released.

2: When a micro-vibration load is applied by a finger in a perpendicular direction, some fibers included in the film are released.

3: A film is not released by a load in the perpendicular direction, but is almost completely released when a shear force is applied in a parallel direction.

4: A film is not released by a load in the perpendicular direction, but a part of the film or some of the fibers are released when a shear force is applied by a finger in a parallel direction.

5: A film is not released by a load in the perpendicular direction, and the film or fibers are not released even when a shear force is applied in a parallel direction.

TABLE 4

| | Component (% by mass) | Example 3-1 | Example 3-2 | Example 3-3 | Example 3-4 | Example 3-5 | Example 3-6 |
|---|---|---|---|---|---|---|---|
| (a) | Ethanol | 79.5 | 79.5 | 79.2 | 66.3 | 66.7 | 42.5 |
| | 1-Butanol | | | | | | 31.5 |
| | 2-Propanol | | | | | | |
| (b) | Polyvinyl butyral | 14 | | 14 | 10 | 10 | |
| | Polyvinylacetal diethylaminoacetate | | 14 | | | | |
| | Alkyl acrylate/octylacrylamide copolymer | | | | | | 20.5 |
| (c) | Water | 0.5 | 0.5 | 0.8 | 0.7 | 0.3 | 0.5 |
| Other component | Di(phytosteryl/octyldodecyl) lauroyl glutamate | 6 | 6 | 6 | | | |
| | Glycerol | | | | 23 | | |
| | Polyglyceryl-2 diisostearate | | | | | 23 | 5 |
| | Total amount | 100.0 | 100.0 | 100.0 | 100.0 | 100.0 | 100.0 |
| Content mass ratio | Component (a)/component (c) | 159.0 | 159.0 | 99.0 | 94.7 | 222.3 | 148.0 |
| | Component (b)/component (c) | 28.0 | 28.0 | 17.5 | 14.3 | 33.3 | 41.0 |
| | Insulating property evaluation | ○ | ○ | ○ | ○ | ○ | ○ |
| | Spinning performance evaluation | ○ | ○ | ○ | ○ | ○ | ○ |
| | Adhesion evaluation | 4 | 4 | 4 | 4 | 4 | 3 |

As apparent from the results shown in Table 4, the electrostatic spray device of the present invention having the structure shown in FIG. 5 and FIG. 6 has high insulating properties and can perform stable spinning. The films formed in Examples are revealed to have high adhesion to the skin model.

Examples 4-1 to 4-9

The liquid compositions of Example 4-1 to 4-9 were prepared in a similar manner to that in Example 2-1 except that the components (a), (b), (c), and (d) and another component were mixed at ratios shown in Table 5. The mixing ratios are shown in Table 5. The electrostatic spraying method was performed in a similar manner to that in Example 2-1 except the following conditions.

The electrostatic spraying method was performed in the following conditions.

Applied voltage: 10 kV
Distance between the nozzle and the skin model: 80 mm
Liquid composition ejection speed: 5 mL/h
Environment: 30° C., 70% RH

[Viscosity Evaluation]

Each liquid composition of Examples 4-1 to 4-9 produced in accordance with a formulation shown in Table 5 was allowed to stand at 25° C. for 24 hours, and then the viscosity was determined by using an E-type viscometer at 25° C. As the E-type viscometer, an E-type viscometer (VISCONIC EMD) manufactured by Tokyo Keiki was used with a rotor No. 43 at a rotation rate of 20 rpm. For a composition having a viscosity of 150 mPa·s or more, measurement was performed at a rotation rate of 10 rpm. Table 5 shows the test results.

[Conductivity Evaluation]

Each liquid composition of Examples 4-1 to 4-9 produced in accordance with a formulation shown in Table 5 was allowed to stand at 25° C. for 24 hours, and then the conductivity was determined by using an impedance analyzer (SI1260, manufactured by Solartron) with a measurement terminal (SH-Z) in conditions of 25° C., 010 mm, and a distance of 1 mm. Table 5 shows the test results.

[Spray Performance Evaluation]

The spray performance of a liquid composition was evaluated by using an electrostatic spray device. Table 5 shows the test results.

A: Spinning is stable, and a film is satisfactory formed.
B: At spinning, fibers are slightly fluffy. A film can be formed.
C: At spinning, fibers are fluffy. A film can be barely formed.
D: At spinning, fibers are so fluffy as to be dispersed around. A film is difficult to form.

TABLE 5

| | Component (% by mass) | Example 4-1 | Example 4-2 | Example 4-3 | Example 4-4 | Example 4-5 | Example 4-6 | Example 4-7 | Example 4-8 | Example 4-9 |
|---|---|---|---|---|---|---|---|---|---|---|
| (a) | Ethanol | 88.55 | 88.46 | 88.06 | 86.56 | 82.29 | 84.08 | 88.26 | 88.06 | 79.83 |
| (b) | Polyvinyl butyral (*1) | 11 | 11 | 11 | 11 | 12 | 15 | 11 | 11 | 11 |
| (c) | Water | 0.44 | 0.44 | 0.44 | 0.44 | 0.41 | 0.42 | 0.44 | 0.44 | 8.87 |
| (d) | Distearyldimonium chloride (*2) | 0.01 | 0.1 | 0.5 | 2 | 0.5 | 0.5 | | | |
| | Benzalkonium chloride (*3) | | | | | | | 0.3 | | 0.3 |
| | Sodium palmitoyl sarcosinate (*4) | | | | | | | | 0.5 | |
| Other component | Di(phytosteryl/octyldodecyl) lauroyl glutamate (*5) | | | | | 4.8 | | | | |
| | Total amount | 100.00 | 100.00 | 100.00 | 100.00 | 100.00 | 100.00 | 100.00 | 100.00 | 100.00 |
| Content mass ratio | Component (b)/component (c) | 25 | 25 | 25 | 25 | 29 | 36 | 25 | 25 | 1 |
| | Component (b)/component (a) | 0.12 | 0.12 | 0.12 | 0.13 | 0.15 | 0.18 | 0.12 | 0.12 | 0.14 |
| | Component (d)/component (c) | 0.02 | 0.23 | 1.14 | 4.55 | 1.22 | 1.19 | 0.68 | 1.14 | 0.03 |
| | Viscosity [mPa·s] (X) | 84 | 88 | 88 | 87 | 110 | 256 | 92 | 83 | 99 |
| | Conductivity[μS/cm] (Y) | 10 | 36 | 90 | 257 | 90 | 95 | 109 | 97 | 110 |
| | Conductivity (Y)/viscosity (X) | 0.12 | 0.41 | 1.02 | 2.95 | 0.82 | 0.37 | 1.18 | 1.17 | 1.11 |
| | Spray performance evaluation | C | A | A | B | A | A | A | A | A |

(*1) S-LEC B BM-1 (SEKISUI CHEMICAL CO., LTD.)
(*2) VARISOFT TA100 (Evonik Japan)
(*3) NIKKOL CA101 (50% aqueous solution/effective amount in Table) (Nikko Chemicals)
(*4) NIKKOL Sarcosinate PN (Nikko Chemicals)
(*5) Eldew PS-203 (Ajinomoto Co., Inc.)

As shown in Table 5, the liquid compositions of Examples 4-1 to 4-9 enables the formation of films even in an environment at a humidity of 70% RH as compared with the liquid compositions of Reference Examples 10 to 12. It is particularly revealed that the liquid compositions of Examples 4-2 to 4-9 were able to be satisfactory sprayed to form films.

INDUSTRIAL APPLICABILITY

According to the present invention, a film having a stable quality can be produced on skin independent of variation in ambient environment including humidity, while the insulating properties are ensured at the time of use of an electrostatic spray device.

The invention claimed is:
1. A method for producing a film, the method comprising:
   electrostatically spraying a liquid composition directly on a surface of skin to form the film on the skin by using an electrostatic spray device, wherein
   the electrostatic spray device includes:
     a container capable of storing the liquid composition,
     a nozzle configured to eject the liquid composition, and
     a power supply configured to apply a voltage to the nozzle;

the liquid composition contains component (a), component (b), and component (c):
(a) one or two or more volatile substances selected from alcohols and ketones,
(b) a water-insoluble polymer having film formability, and
(c) 0.2% by mass or more and 25% by mass or less of water;
in said electrostatic spraying;
the electrostatic spray device is held by hand,
the power supply applies a voltage of 5 kV or more and 50 kV or less to the nozzle that ejects the liquid composition at a flow rate of 0.4 mL/h or more and 30 mL/h or less to perform electrostatic spraying on the surface of the skin; and
a ratio of the flow rate to the voltage is 0.8 or less;
the electrostatic spray device includes:
a cartridge, and
a main body;
the cartridge includes the container and the nozzle configured to eject the liquid composition from the container;
the main body includes:
the power supply configured to apply the voltage to the nozzle,
a power source configured to drive a pump to eject the liquid composition, and
a power transmitter configured to transmit a motive power from the power source to the cartridge;
the power transmitter electrically insulates the power source from the cartridge; and
the cartridge is detachable from the main body.

2. The method for producing the film according to claim 1, wherein, in said electrostatic spraying, the liquid composition has a viscosity at 25° C. of 5 mPa·s or more and 3,000 mPa·s or less.

3. The method for producing the film according to claim 1, wherein, in said electrostatic spraying, a distance between the nozzle and the skin is 10 mm or more and 160 mm or less.

4. The method for producing the film according to claim 1, wherein, in said electrostatic spraying, the film has a basis weight of 0.05 g/m² or more and 50 g/m² or less relative to 1 m² of the skin.

5. The method for producing the film according to claim 1, wherein, in said electrostatic spraying, the liquid composition is electrostatically sprayed on skin to form a porous film including deposited fibers.

6. The method for producing the film according to claim 1, further comprising:
applying, onto the skin, a liquid agent containing one or two or more substances selected from water, a polyol, and an oil that is liquid at 20° C.,
wherein the liquid agent differs from the liquid composition.

7. A method for producing a film, the method comprising:
electrostatically spraying a liquid composition directly on a surface of skin to form the film on the skin by using an electrostatic spray device, wherein
the electrostatic spray device includes:
a cartridge,
a main body, and
a power supply configured to apply a voltage to a nozzle;
the cartridge includes:
a container capable of storing the liquid composition, and
the nozzle configured to eject the liquid composition;
the main body includes:
a power source configured to drive a pump to eject the liquid composition, and
a power transmitter configured to transmit a motive power from the power source to the pump;
the power transmitter electrically insulates the power source from the cartridge;
the cartridge is detachable from the main body;
the liquid composition contains component (a), component (b), and component (c):
(a) one or two or more volatile substances selected from alcohols and ketones,
(b) a water-insoluble polymer having film formability, and
(c) 0.2% by mass or more and 25% by mass or less of water; and
in said electrostatic spraying:
the power supply applies a voltage of 5 kV or more and 50 kV or less to the nozzle that ejects the liquid composition at a flow rate of 0.4 mL/h or more and 30 mL/h or less to perform electrostatic spraying on the surface of the skin, and
a ratio of the flow rate to the voltage is 0.8 or less.

8. The method for producing the film according to claim 7, wherein
the component (b) is capable of being dissolved in the component (a),
the component (b) is capable of forming a film including deposited fibers,
the content of the component (b) in the liquid composition is 5% by mass or more and 40% by mass or less, and
the content of the component (a) in the liquid composition is 50% by mass or more and 94% by mass or less.

9. The method for producing the film according to claim 7, wherein the component (b) is at least one selected from the group consisting of a partially saponified polyvinyl alcohol, a low-saponified polyvinyl alcohol, a completely saponified polyvinyl alcohol, a polyvinyl butyral resin, a polymethacrylic acid resin, polyvinylacetal diethylaminoacetate, an oxazoline-modified silicone, and polylactic acid.

10. The method for producing the film according to claim 7, wherein a mass ratio of the content of the component (b) to that of the component (c) is 0.4 or more and 50 or less.

11. The method for producing the film according to claim 7, wherein
the cartridge includes a gasket slidable along an inner surface of the container containing the liquid composition, and
the gasket is slid by a motive power from the power source to eject the liquid composition from the nozzle.

12. The method for producing the film according to claim 7, wherein
the cartridge includes:
a container capable of storing the liquid composition, the container being deformable according to an internal pressure,
the nozzle, and
the pump configured to feed the liquid composition stored in the container to the nozzle; and
the liquid composition is to be ejected from the nozzle by a motive power of the pump transmitted from the power source.

13. The method for producing the film according to claim 7, wherein
the nozzle has a microspace through which the liquid composition passes; and the microspace has a cross-sectional diameter of 100 μm or more and 1,400 μm or less.

14. The method for producing the film according to claim 7, wherein the nozzle has a flow path length of 1 mm or more and 25 mm or less.

15. The method for producing the film according to claim 7, wherein, in said electrostatic spraying, a distance between the nozzle and the skin is 10 mm or more and 160 mm or less.

16. The method for producing the film according to claim 7, further comprising:
- applying, onto the skin, a liquid agent containing one or two or more substances selected from water, a polyol, and an oil that is liquid at 20° C.,
- wherein the liquid agent differs from the liquid composition.

* * * * *